(12) United States Patent
Mourich et al.

(10) Patent No.: US 8,008,469 B2
(45) Date of Patent: *Aug. 30, 2011

(54) ANTISENSE COMPOUND FOR INDUCING IMMUNOLOGICAL TOLERANCE

(75) Inventors: Dan V. Mourich, Albany, OR (US); Hong M. Moulton, Corvallis, OR (US); David J. Hinrichs, Lake Oswego, OR (US); Patrick L. Iversen, Corvallis, OR (US)

(73) Assignee: AVI BioPharma Inc., Corvallis, OR (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/941,033

(22) Filed: Nov. 15, 2007

(65) Prior Publication Data

US 2009/0111977 A1   Apr. 30, 2009

Related U.S. Application Data

(63) Continuation of application No. 10/946,881, filed on Sep. 22, 2004, now abandoned.

(60) Provisional application No. 60/505,418, filed on Sep. 23, 2003.

(51) Int. Cl.
- *C07H 21/02* (2006.01)
- *C07H 21/04* (2006.01)
- *C12Q 1/68* (2006.01)
- *A61K 31/70* (2006.01)

(52) U.S. Cl. ......... 536/24.5; 435/6; 536/23.1; 536/24.1; 514/44 A

(58) Field of Classification Search ........................... None
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,576,302 A | 11/1996 | Cook et al. |
| 5,580,767 A | 12/1996 | Cowsert et al. |
| 5,698,685 A | 12/1997 | Summerton et al. |
| 5,702,891 A | 12/1997 | Kolberg et al. |
| 5,733,781 A | 3/1998 | Ryder et al. |
| 5,734,039 A | 3/1998 | Calabretta et al. |
| 5,801,154 A | 9/1998 | Baracchini et al. |
| 5,849,727 A | 12/1998 | Porter et al. |
| 5,892,023 A | 4/1999 | Pirotzky et al. |
| 5,955,318 A | 9/1999 | Simons et al. |
| 6,060,456 A | 5/2000 | Arnold et al. |
| 6,133,246 A | 10/2000 | McKay et al. |
| 6,174,868 B1 | 1/2001 | Anderson et al. |
| 6,210,892 B1 | 4/2001 | Bennett et al. ................. 435/6 |
| 6,228,579 B1 | 5/2001 | Zyskind et al. |
| 6,239,265 B1 | 5/2001 | Cook |
| 6,306,993 B1 | 10/2001 | Rothbard et al. |
| 6,365,351 B1 | 4/2002 | Iversen |
| 6,495,663 B1 | 12/2002 | Rothbard |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 7,049,431 B2 | 5/2006 | Iversen et al. |
| 7,094,765 B1 | 8/2006 | Iversen et al. |
| 7,115,374 B2 | 10/2006 | Linnen et al. |
| 7,468,418 B2 | 12/2008 | Iversen et al. ................. 530/300 |
| 2002/0049173 A1 | 4/2002 | Bennett et al. ................. 514/44 |
| 2002/0127198 A1 | 9/2002 | Rothbard et al. |
| 2003/0166588 A1 | 9/2003 | Iversen et al. |
| 2003/0171335 A1 | 9/2003 | Stein et al. |
| 2003/0224353 A1 | 12/2003 | Stein et al. |
| 2004/0254137 A1* | 12/2004 | Ackermann et al. ........... 514/44 |
| 2004/0259108 A1 | 12/2004 | Linnen et al. |
| 2004/0265879 A1* | 12/2004 | Iversen et al. ................. 435/6 |
| 2005/0176661 A1 | 8/2005 | Vaillant et al. |
| 2005/0203041 A1 | 9/2005 | Mourich et al. |
| 2005/0234002 A1 | 10/2005 | Mourich et al. |
| 2006/0149046 A1 | 7/2006 | Arar |
| 2006/0269911 A1* | 11/2006 | Iversen et al. ................. 435/5 |
| 2006/0276425 A1* | 12/2006 | Mourich et al. ............... 514/44 |
| 2007/0122821 A1* | 5/2007 | Iversen et al. ................. 435/6 |

(Continued)

FOREIGN PATENT DOCUMENTS

EP   0 403 333 A2   12/1990

(Continued)

OTHER PUBLICATIONS

Irmler et al. (1997) Nature 388(6638):190-5.*

(Continued)

*Primary Examiner* — Sean McGarry
(74) *Attorney, Agent, or Firm* — Seed IP Law Group PLLC

(57) ABSTRACT

A method and conjugate for selectively killing antigen-activated T cells are disclosed. The conjugate is composed of a substantially uncharged antisense compound targeted against the human cFLIP protein, and a reverse TAT (rTAT) polypeptide coupled covalently to the antisense compound. The rTAT polypeptide is effective to produce selective uptake of the conjugate into antigen-activated T cells, relative to the uptake of the conjugate into non-activated T cells. The cFLIP antisense compound causes activation induced cell death (AICD) of activated lymphocytes. The method is useful in treating transplantation rejection and autoimmune conditions.

10 Claims, 7 Drawing Sheets

U.S. PATENT DOCUMENTS

| | | | |
|---|---|---|---|
| 2009/0082547 A1 | 3/2009 | Iversen et al. | 530/322 |
| 2009/0088562 A1 | 4/2009 | Weller et al. | 536/24.5 |
| 2009/0099066 A1 | 4/2009 | Moulton et al. | 514/7 |
| 2009/0110689 A1 | 4/2009 | Mourich et al. | 424/184.1 |
| 2009/0246221 A1 | 10/2009 | Mourich et al. | 424/194.1 |
| 2010/0184670 A1 | 7/2010 | Mourich et al. | 514/12 |

FOREIGN PATENT DOCUMENTS

| | | |
|---|---|---|
| FR | 2647809 | 6/1989 |
| WO | WO 90/07936 A1 | 7/1990 |
| WO | WO 91/05864 A1 | 5/1991 |
| WO | WO 95/05851 A1 | 3/1995 |
| WO | WO 0071706 A1 * | 11/2000 |
| WO | WO 01/72765 | 10/2001 |
| WO | WO 2009/086469 | 7/2009 |
| WO | WO 2010/080554 | 7/2010 |

OTHER PUBLICATIONS

Agrawal et al.,"Site-specific excision from RNA by RNase H and mixed-phosphate-backbone oligodeoxynucleotides." *Proc Natl Acad Sci U S A*, 87(4): 1401-5 (1990).

Agrawal et al., *TIBTECH*, 14:376-387 (1996).

Agrawal et al., *Molecular Medicine Today*, 61:72-81 (2000).

Akhtar, S., et al., *Nucleic Acids Res*, 19(20):5551-9 (1991).

Anderson, C. M., et al., *J Neurochem*, 73(2):867-73 (1999).

Anderson, K. P., et al., *Antimicrob Agents Chemother*, 40(9):2004-11 (1996).

Bonham et al., "An assessment of the antisense properties of RNase H-competent and steric-blocking oligomers." *Nucleic Acids Res* 23(7): 1197-203 (1995).

Boudvillain et al., "Transplatin-modified oligo(2'-O-methyl ribonucleotide)s: a new tool for selective modulation of gene expression." *Biochemistry*, 36(10): 2925-31 (1997).

Branch, *TIBS*, 23:45-49 (1998).

Braasch et al., *Biochemistry*, 41:4503-4510 (2002).

Chen et al., *Bioconjugate Chem.*, 14:532-538 (2003).

Choudhury, I. et al., *Journal of Acquired Immune Deficiency Syndromes and Human Retrovirology*, 17(2): 104-111, 1998.

Ding, D., et al., *Nucleic Acids Res.*, 24(2):354-60 (1996).

Gee, J. E., et al., *Antisense Nucleic Acid Drug Dev.*, 8(2)103-11 (1998).

Hudziak, R. M., et al., *Antisense Nucleic Acid Drug Dev.*, 6(4):267-72 (1996).

Loke, S. L., et al., *Proc Natl Acad Sci USA*, 86(10):3474-8 (1989).

Micheau, *Expert Opin. Ther. Targets*, 7:559-573 (2003).

Moulton, H. M., et al., *Antisense Nucleic Acid Drug Dev.*, 13(1):31-43 (2003).

Moulton, H. M. and J. D. Moulton, *Curr Opin Mol Ther.*, 5(2):123-32 (2003).

Murphy et al., *Science*, 250(4988)1720-1723 (1990).

Pari, G. S., et al., *Antimicrob Agents Chemother.*, 39(5):1157-61 (1995).

Stein, D., et al., *Antisense Nucleic Acid Drug Dev.*, 7(3):151-7 (1997).

Summerton, J. and D. Weller (1997). "Morpholino antisense oligomers: design, preparation, and properties." *Antisense Nucleic Acid Drug Dev.*, 7(3):187-95.

Toulme, J. J., R. L. Tinevez, et al. (1996). "Targeting RNA structures by antisense oligonucleotides." *Biochimie*, 78(7):663-73.

Wasem et al., *J. Clin. Invest.*, 111(8):1191-1199 (2003).

Vanin, E.F. and Ji, T.H., *Biochemistry*, 20:6754-6760 (1981).

Tung, C. et al., *Bioconjugate Chem.*, 6:292-295, 1995.

Wender, P. A., et al., *Proc Natl Acad Sci USA*, 97(24):13003-8 (2000).

Yakubov, L. A., et al., *Proc Natl Acad Sci USA*, 86(17):6454-8 (1989).

Zhu et al., *J. Virology*, 76(2):707-716 (2002).

Agrawal et al., "Antisense Therapeutics: Is it as Simple as Complementary Bse Recognition?", *Molecular Medicine Today*, 6:72-81 (2000).

Agrawal et al.,"Oligodeoxynucleoside phosphoramidates and phosphorothioates as inhibitors of human immunodeficiency virus", *Proc Natl Acad Sci U S A*, 85(19):7079-7083 (1988).

Agrawal et al.,"Site-specific excision from RNA by RNase H and mixed-phosphate-backbone oligodeoxynucleotides", *Proc Natl Acad Sci U S A*, 87(4): 1401-5 (1990).

Agrawal, S., "Antisense oligonucleotides: towards clinical trials", *TIBTECH*, 14:376-387 (1996).

Akhtar, S., et al., "Interactions of antisense DNA oligonucleotide analogs with phospholipid membranes (liposomes)", *Nucleic Acids Res*, 19(20):5551-9 (1991).

Anderson, C. M., et al., "Distribution of equilibrative, nitrobenzylthioinosine-sensitive nucleoside transporters (ENT1) in brain", *J Neurochem*, 73(2):867-73 (1999).

Anderson, K. P., et al., "Inhibition of human cytomegalovirus immediate-early gene expression by an antisense oligonucleotide complementary to immediate-early RNA", *Antimicrob Agents Chemother*, 40(9):2004-11 (1996).

Arora et al., "Bioavailability and efficacy of antisense morpholino oligomers targeted to c-myc and cytochrome P-450 3A2 following oral administration in rats", *Journal of Pharmaceutical Sciences*, 91(4):1009-1018 (2002).

Astriab-Fisher et al., "Conjugates of antisense oligonucleotides with the Tat and antennapedia cell-penetrating peptides: effects on cellular uptake, binding to target sequences, and biologic actions", *Pharm. Res.*, 19(6):744-754 (2002).

Bailey, C. P., J. M. Dagle et al., "Cationic oligonucleotides can mediate specific inhibition of gene expression in *Xenopus* oocytes." *Nucleic Acids Res*, 26(21): 4860-7 (1998).

Barawkar, D. A. and T. C. Bruice "Synthesis, biophysical properties, and nuclease resistance properties of mixed backbone oligodeoxynucleotides containing cationic internucleoside guanidinium linkages: deoxynucleic guanidine/DNA chimeras", *Proc Natl Acad Sci U S A.*, 95(19):11047-11052 (1998).

Bonham et al., "An assessment of the antisense properties of RNase H-competent and steric-blocking oligomers", *Nucleic Acids Res* 23(7): 1197-203 (1995).

Boudvillain et al., "Transplatin-modified oligo(2'-O-methyl ribonucleotide)s: a new tool for selective modulation of gene expression." *Biochemistry*, 36(10): 2925-31 (1997).

Braasch, D.A. and Corey, D.R., "Novel antisense and peptide nucleic acid strategies for controlling gene expression", *Biochemistry*, 41:4503-4510 (2002).

Branch, Andrea D., "A good antisense molecule is hard to find", *Trends in Biochem. Sci.*, 23:45-50 (1998).

Braun, et al., "Setting the stage for bench-to-bedside movement of anti-HIV RNA inhibitors—gene therapy for AIDS in macaques", *Frontier Biosciences*, 11:838-851 (2006).

Chen et al., "A concise method for the preparation of peptide and arginine-rich peptide-conjugated antisense oligonucleotide", *Bioconjugate Chemistry.*, 14:532-538 (2003).

Chirilla et al., "The use of synthetic polymers for delivery of therapeutic antisense oligodeoxynucleotides", *Biomaterials*, 23(2):321-342 (2002).

Choudhury, I. et al., *Journal of Acquired Immune Deficiency Syndromes and Human Retrovirology*, 17(2):104-111, 1998.

Courcoul et al., "Peripheral blood mononuclear cells produce normal amounts of defective Vif—human immunodeficiency virus type 1 particles which are restricted for the preretrotranscription steps", *Journal of Virology*, 69(4):2068-2074 (1995).

Crooke, S. T., Antisense Drug Technology: Basic Principles of Antisense Technology. New York, Marcel Dekker, S. Crooke Ed Springer pp. 1-28 (2001).

Crooke, S. T., Antisense Drug Technology: Principles, Strategies, and Applications. New York, Marcel Dekker, S. Crooke Ed Springer pp. 1-50 (1999).

Desrosiers et al., "Identification of highly attenuated mutants of simian immunodeficiency virus", *Journal of Virology*, 72(2):1431-1437 (1998).

Desrosiers, R.C., "HIV with multiple gene deletions as a live attenuated vaccine for AIDS", *AIDS Research and Human Retroviruses*, 8(3):411-421 (1992).

Dettenhofer et al., "Association of human immunodeficiency virus type 1 Vif with RNA and its role in reverse transcription", *Journal of Virology*, 74(19):8938-8945 (2000).

Ding, D., et al., "An oligodeoxyribonucleotide N3'→P5' phosphoramidate duplex forms an A-type helix in solution", *Nucleic Acids Res.*, 24(2):354-60 (1996).

Fanning et al. "Gene therapy for HIV/AIDS: the potential for a new therapeutic regimen", *The Journal of Gene Medicine*, 5:645-653 (2003).

Gee et al., "Assessment of high-affinity hybridization, RNase H cleavage, and covalent linkage in translation arrest by antisense oligonucleotides", *Antisense Nucleic Acid Drug Dev.*, 8(2):103-11 (1998).

Gewirtz, A.M. et al., "Facilitating oligonucleotide delivery: helping antisense deliver on its promise", *Proc. Natl. Acad. Sci. U.S.A.*, 93(8):3161-3163 (1996).

Gilbert et al., "Sieve analysis: methods for assessing from vaccine trial data how vaccine efficacy varies with genotypic and phenotypic pathogen variation", *Journal of Clinical Epidemiology*, 54:68-85 (2001).

Goncalves et al., "Role of Vif in human immunodeficiency virus type 1 reverse transcription", *Journal of Virology*, 70(12):8701-8709 (1996).

Green, D.W. et al., "Antisense oligonucleotides: an evolving technology for the modulation of gene expression in human disease", *Journal of American College of Surgeons*,191(1): 93-105():(2000).

Harris et al., "DNA deamination mediates innate immunity to retroviral infection", *Cell*, 113(6):803-809 (2003).

Huang, S. et al. "A polyethylene glycol copolymer for carrying and releasing multiple copies of cysteine-containing peptides", *Bioconjgate Chemistry*, 9(5):612-617 (1998).

Hudziak, R.M et al., "Resistance of morpholino phosphorodiamidate oligomers to enzymatic degradation", *Antisense Nucleic Acid Drug Dev.*, 6:267-272 (1996).

Jen et al., "Suppression of gene expression by targeted disruption of messenger RNA: available options and current strategies", *Stem Cells*, 18:307-319 (2000).

Kinter et al., "HIV envelope induces virus expression from resting CD4+ T cells isolated from HIV-infected individuals in the absence of markers of cellular activation or apoptosis", *Journal of Immunology*, 170(5):2449-2455 (2003).

Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11):1893-1901 (2000).

Lisziewicz et al., "Specific inhibition of human immunodeficiency virus type 1 replication by antisense oligonucleotides: an in vitro model for treatment", *Proc. Natl. Acad. Sci.*, 89:11209-11213 (1992).

Loke et al., "Characterization of oligonucleotide transport into living cells", *Proc. Natl. Acad. Sci.*, 86(10):3474-3478 (1989).

Lu et al., "Antisense-mediated inhibition of human immunodeficiency virus (HIV) replication by use of an HIV type 1-based vector results in severely attenuated mutants incapable of developing resistance", *Journal of Virology*, 78(13):7079-7088 (2004).

Mariani et al., "Species-specific exclusion of APOBEC3G from HIV-1 virions by Vif", *Cell*, 114(1):21-31 2003.

Marin et al., "HIV-1 Vif protein binds the editing enzyme APOBEC3G and induces its degradation", *Nature Medicine*, 9(11):1398-1403 (2003).

Micklefield, J., "Backbone modification of nucleic acids: synthesis, structure and therapeutic applications." *Curr Med Chem.*, 8(10):1157-79 (2001).

Micheau, O., "Cellular FLICE-inhibitory protein: an attractive therapeutic target?", *Expert Opin. Ther. Targets*, 7:559-573 (2003).

Moulton et al., "HIV Tat peptide enhances cellular delivery of antisense morpholino oligomers", *Antisense Nucleic Acid Drug Dev.*, 13:31-43 (2003).

Moulton, H. M. and J. D. Moulton, "Peptide-assisted delivery of steric-blocking antisense oligomers", *Curr Opin Mol Ther.*, 5(2):123-32 (2003).

Moulton, H. M., M. H. Nelson, et al., "Cellular uptake of antisense morpholino oligomers conjugated to arginine-rich peptides." *Bioconjugate Chemistry*, 15(2):290-9 (2004).

Murphy et al., "Induction by antigen of intrathymic apoptosis of CD4+CD8+TCRIo thymocytes in vivo", *Science*, 250(4988):1720-1723 (1990).

Opalinska, J.B. and Gewirtz, A.M., "Nucleic-acid therapeutics: basic principles and recent applications", *Nature Reviews/Drug Discovery*, 1:503-514 (2002).

Palu, et al., "In pursuit of new developments for gene therapy of human diseases", *Journal of Biotechnology*, 68(1):1-13 (1999).

Pari et al., "Potent antiviral activity of an antisense oligonucleotide complementary to the intron-exon boundary of human cytomegalovirus genes UL36 and UL37", *Antimicrobial Agents and Chemotherapy*, 39(5):1157-1161 (1995).

Rittner, K and Sczakiel, G, "Identification and analysis of antisense RNA target regions of the human immunodeficiency virus type 1", *Nucleic Acids Research*, 19(7):1421-1426 (1991).

Rothbard et al., "Arginine-rich molecular transporters for drug delivery: role of backbone spacing in cellular uptake", *J. Med. Chem.*, 45:3612-3618 (2002).

Schubert, et al., "Oligonucleotide-based antiviral strategies", *HEP*, 173:261-287 (2006).

Sheehy et al., "Isolation of a human gene that inhibits HIV-1 infection and is suppressed by the viral Vif protein", *Nature*, 418(6898):646-650 (2001).

Simon et al., "The human immunodeficiency virus type 1 Vif protein modulates the postpenetration stability of viral nucleoprotein complexes", *Journal of Virology*, 70(8):5297-5305 (1996).

Stein, D., et al., "A specificity comparison of four antisense types: morpholino, 2'-O-methyl RNA, DNA, and phosphorothioate DNA", *Antisense & Nucleic Acid Drug Development*, 7(3):151-7 (1997).

Summerton et al., "Morpholino and phosphorothioate antisense oligomers compared in cell-free and in-cell systems", *Antisense & Nucleic Acid Drug Development*, 7:63-70 (1997).

Summerton et al., "Morpholino antisense oligomers: the case for an RNase H-independent structural type", *Biochim et. Biophys. ACTA*, 1489:141-158 (1999).

Suzuki et al., "Possible existence of common internalization mechanisms among arginine-rich peptides", *Journal of Biological Chemistry*, 277(4):2437-2443 (2002).

Tamm et al, "Antisense therapy in oncology: new hope for an old idea?", *The Lancet*, 358(9280):489-497 (2001).

Tondelli et al., "Native oligodeoxynucleotides specifically active against human immunodeficiency virus type 1 in vitro: a G-quartet-driven effect?", *Antimicrobial Agents and Chemotehrapy*, 40(9):2034-2038 (1996).

Torrence et al., "Targeting RNA for degradation with a (2'-5')oligoadenylate-antisense chimera", *Proc. Natl. Acad. Sci U.S.A.*, 90:1300-1304 (1993).

Toulme, J. J., R. L. Tinevez, et al., "Targeting RNA structures by antisense oligonucleotides." *Biochimie*, 78(7):663-73 (1996).

Tung, C. et al.,"Dual-specificity interaction of HIV-1 TAR RNA with Tat peptide-oligonucleotide conjugates", *Bioconjugate Chem.*, 6:292-295, 1995.

Vanin, E.F. and Ji, T.H., "Synthesis and application of cleavable photoactivable heterobifunctional reagents", *Biochemistry*, 20:6754-6760 (1981).

Vives et al., "A truncated HIV-1 Tat protein basic domain rapidly translocates through the plasma membrane and accumulates in the cell nucleus", *Journal of Biological Chemistry*, 272(25):16010-16017 (1997).

Wasem et al.,"Sensitizing antigen-specific CD8+ T cells for accelerated suicide causes immune incompetence", *J. Clin. Invest.*, 111(8):1191-1199 (2003).

Wender, P. A., et al., "The design, synthesis, and evaluation of molecules that enable or enhance cellular uptake: peptoid molecular transporters", *Proc Natl Acad Sci U S A*, 97(24):13003-8 (2000).

Wolkowicz, et al., "Gene therapy progress and prospects: novel gene therapy approaches for AIDS", *Gene Therapy*, 12(6):467-476 (2005).

Yakubov, L.A., et al., "Mechanism of oligonucleotide uptake by cells: involvement of specific receptors?", *Proc Natl Acad Sci U S A.*, 86(17):6454-8 (1989).

Zhu et al., "Evidence for human immunodeficiency virus type 1 replication in vivo in CD14(+) monocytes and its potential role as a source of virus in patients on highly active antiretroviral therapy", *Journal of Virology*, 76(2):707-716 (2002).

Bielekova, B. et al., :"Expansion and functional relevance of high-avidity myelin-specific CD4+ T cells in multiple sclerosis", *The Journal of Immunology*, 172(6):3893-3904 (2004).

Bielekova, B. et al., "Encephalitogenic potential of the myelin basic protein peptide (amino acids 83-99) in multiple sclerosis: results of a phase II clinical trial with an altered peptide ligand", *Nature Medicine*, 6(10):1167-1175 (2000).

Bracci, L. et al., "Synthetic peptides in the form of dendrimers become resistant to protease activity", *The Journal of Biological Chemistry*, 278(47):46590-46595 (2003).

Burrows, G. et al., "Regulation of encephalitogenic T cells with recombinant TCR ligands", *The Journal of Immunology*, 164(12):6366-6371 (2000).

Burrows, G. et al., "Two-domain MHC class II molecules form stable complexes with myelin basic protein 69-89 peptide that detect and inhibit rat encephalitogenic T cells and treat experimental autoimmune encephalomyelitis", *The Journal of Immunology*, 161(11):5987-5996 (1998).

Daniel, D. and Wegmann, D., "Protection of nonobese diabetic mice from diabetes by intranasal or subcutaneous administration of insulin peptide B-(9-23)" *Proc. Natl. Acad. Sci. USA*, 93(2):956-960 (1996).

De Rosbo et al., "The myelin-associated oligodendrocytic basic protein region MOBP15-36 encompasses the immunodominant major encephalitogenic epitope(s) for SJL/J mice and predicted epitope(s) for multiple sclerosis-associated HLA-DRB1*1501", *The Journal of Immunology*, 173(2):1426-1435 (2004).

Ellis, H.J. et al., "Investigation of the putative immunodominant T cell epitopes in coeliac disease", *Gut*, 52(2):212-217 (2003).

Falk, K. et al., "Induction and suppression of an autoimmune disease by oligomerized T cell epitopes: enhanced in vivo potency of encephalitogenic peptides", *J. Exp. Med.*, 191(4):717-730 (2000).

Fraser, J.S. et al., "Coeliac disease: in vivo toxicity of the putative immunodominant epitope", *Gut*, 52(12):1698-1702 (2003).

Fujii et al., "The linkage of innate to adaptive immunity via maturing dendritic cells in vivo requires CD40 ligation in addition to antigen presentation and CD80/86 costimulation", *J. Exp. Med.*, 199(12):1607-1618 (2004).

Hawiger et al., "Dendritic cells induce peripheral T cell unresponsiveness under steady state conditions in vivo", *J. Exp. Med.*, 194(6):769-779 (2001).

Holz, A. et al., "Myelin-associated oligodendrocytic basic protein: identification of an encephalitogenic epitope and association with multiple sclerosis", *The Journal of Immunology*, 164:1103-1109 (2000).

Huan, J. et al., "Monomeric recombinant TCR ligand reduces relapse rate and severity of experimental autoimmune encephalomyelitis in SJL/J mice through cytokine switch", *The The Journal of Immunology*, 172:4556-4566 (2004).

Hudziak, R.M. et al., "Antiproliferative effects of steric blocking phosphorodiamidate morpholino antisense agents directed against c-myc", *Antisense & Nucleic Acid Drug Development*, 10(3):163-176 (2000).

Jones, D.A. et al., "Identification of autoantigens in psoriatic plaques using expression cloning", *J. of Invest. Dermatol.*, 123:93-100 (2004).

Kappos, L. et al., "Induction of a non-encephalitogenic type 2 T helper-cell autoimmune response in multiple sclerosis after administration of an altered peptide ligand in a placebo-controlled, randomized phase II trial. The Altered Peptide Ligand in Relapsing MS Study Group", *Nature Medicine*, 6(10):1176-1182 (2000).

Lin, M-S. et al., "Development and characterization of desmoglein-3 specific T cells from patients with pemphigus vulgaris", *J. Clin. Invest.*, 99(1):31-40 (1997).

Liu, E. et al., "Anti-peptide autoantibodies and fatal anaphylaxis in NOD mice in response to insulin self-peptides B:9-23 and B:13-23", *The Journal of Clinical Investigation*, 110(7):1021-1027 (2002).

Mantegazzi, R. et al., "Anti-MOG autoantibodies in Italian multiple sclerosis patients: specificity, sensitivity and clinical association", *International Immunology*, 16(3):559-565 (2004).

Nakayama, M. et al., "Prime role for an insulin epitope in the development of type 1 diabetes in NOD mice", *Nature*, 435(7039):220-223 (2005).

Rotzschke, O. et al., "Superactivation of an immune response triggered by oligomerized T cell epitopes", *Proc. Natl. Acad. Sci., USA*, 94:14642-14647 (1997).

Shan, L. et al., "Structural Basis for Gluten Intolerance in Celiac Sprue", *Science*, 297:2275-2279 (1997).

Steinekemeier, M. et al., "Vaccination, prevention, and treatment of experimental autoimmune neuritis (EAN) by an oligomerized T cell epitope", *Proc. Natl. Acad. Sci., USA*, 98(24):13872-13877 (2001).

Vandenbark, A.A. et al., "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice", *The Journal of Immunology*, 171(1):127-133 (2003).

Vanderlugt, C.L. et al., "Pathologic role and temporal appearance of newly emerging autoepitopes in relapsing experimental autoimmune encephalomyelitis", *The Journal of Immunology*, 164(2):670-678 (2000).

Veldman, C. et al., "Dichotomy of autoreactive Th1 and Th2 cell responses to desmoglein 3 in patients with pemphigus vulgaris (PV) and healthy carriers of PV-associated HLA class II alleles", *The Journal of Immunology*, 170(1):635-642 (2003).

Williams, A.S. et al., "A single intra-articular injection of liposomally conjugated methotrexate suppresses joint inflammation in rat antigen-induced arthritis", *British Journal of Rheumatology*, 35(8):719-724 (1996).

You et al., "In vitro RNA synthesis from exogenous dengue viral RNA templates requires long range interactions between 5'- and 3'-terminal regions that influence RNA structure", *The Journal of Biological Chemistry*, 276(19):15581-15591 (2001).

You et al., "Presence of diabetes-inhibiting, glutamic acid decarboxylase-specific, IL-10-dependent, regulatory T cells in naive nonobese diabetic mice", *The Journal of Immunology*, 173(11):6777-6785 (2004).

Yu, M. et al., "A predictable sequential determinant spreading cascade invariably accompanies progression of experimental autoimmune encephalomyelitis: a basis for peptide-specific therapy after onset of clinical disease", *J. of Exp. Med.*, 183(4):1777-1788 (1996).

Zhang, H. and Serrero, G., "Inhibition of tumorigenicity of the teratoma PC cell line by transfection with antisense cDNA for PC cell-derived growth factor (PCDGF, epithelin/granulin precursor)", *Proc. Natl. Acad. Sci., USA*, 95(24):14202-14207 (1998).

Zollinger, W.D. and Moran, E., "Meningococcal vaccines—present and future", *Transactions of Royal Soc of Tropical Medicine and Hygiene*, 85(Supp. 1):37-43 (1991).

International Search Report for International Application No. PCT/US2000/008174, mailed Jul. 25, 2000, 2 pages.

International Search Report for International Application No. PCT/US2008/088339, mailed Jun. 4, 2009, 4 pages.

International Search Report for International Application No. PCT/US2009/068599, mailed May 21, 2010, 3 pages.

Iversen et al., "Compositions for Enhancing Transport of Molecules Into Cells," U.S. Appl. No. 60/466,703, filed Apr. 29, 2003, 55 pages.

Moulton et al., "Compound and Method for Treating Myotonic Dystrophy," U.S. Appl. No. 12/493,140, filed Jun. 26, 2009, 80 pages.

Mourich et al., "Antisense Compound and Method for Selectively Killing Activated T Cells," U.S. Appl. No. 60/505,418, filed Sep. 23, 2003, 60 pages.

* cited by examiner

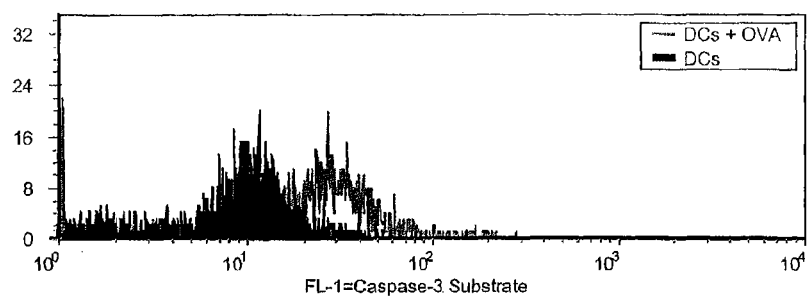
Fig. 6A
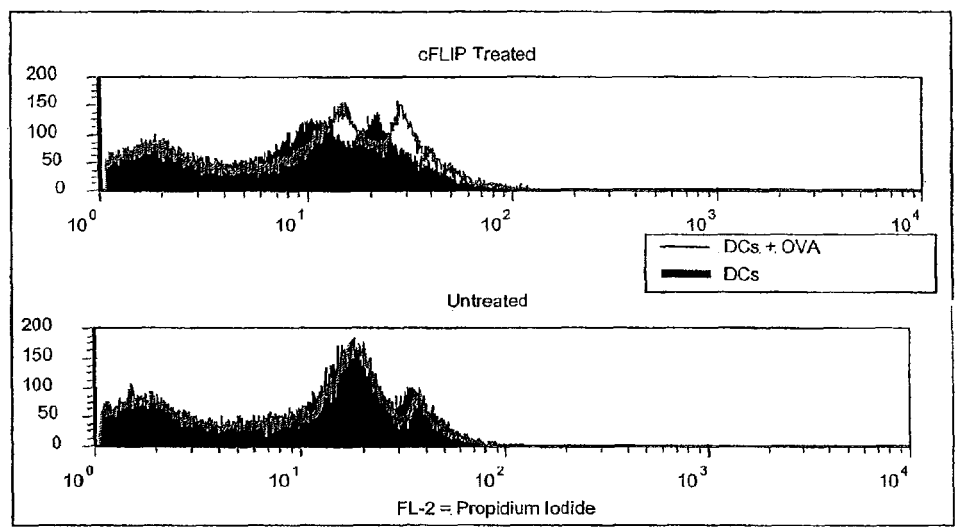
Fig. 6B
Fig. 6C

SEQUENCE LISTING

```
<160> NUMBER OF SEQ ID NOS: 31

<210> SEQ ID NO 1
<211> LENGTH: 10
<212> TYPE: PRT
<213> ORGANISM: Artificial Sequence
<220> FEATURE:
<223> OTHER INFORMATION: The reverse of the TAT sequence of SEQ ID NO:3

<400> SEQUENCE: 1

Arg Arg Arg Gln Arg Arg Lys Lys Arg Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic arginine rich peptide

<400> SEQUENCE: 2

Arg Arg Arg Arg Arg Arg Arg Arg Arg Phe Phe Cys
1               5                   10

<210> SEQ ID NO 3
<211> LENGTH: 10
<212> TYPE: PRT
<213> ORGANISM: Human immunodeficiency virus type 1

<400> SEQUENCE: 3

Arg Lys Lys Arg Arg Gln Arg Arg Arg Cys
1               5                   10

<210> SEQ ID NO 4
<211> LENGTH: 25
<212> TYPE: DNA
```

```
<213> ORGANISM: Homo sapiens

<400> SEQUENCE: 4
tctaagagta ggatgtctgc tgaag                                        25

<210> SEQ ID NO 5
<211> LENGTH: 21
<212> TYPE: DNA
<213> ORGANISM: Homo sapiens

<400> SEQUENCE: 5
ccttgtgagc ttccctagtc t                                            21

<210> SEQ ID NO 6
<211> LENGTH: 21
<212> TYPE: DNA
<213> ORGANISM: Homo sapiens

<400> SEQUENCE: 6
gaagtcatcc atcaggttga a                                            21

<210> SEQ ID NO 7
<211> LENGTH: 19
<212> TYPE: DNA
<213> ORGANISM: Homo sapiens

<400> SEQUENCE: 7
ccttgtttcg gactatagg                                               19

<210> SEQ ID NO 8
<211> LENGTH: 19
<212> TYPE: DNA
<213> ORGANISM: Homo sapiens

<400> SEQUENCE: 8
ggtttgcaga gtgctgatg                                               19

<210> SEQ ID NO 9
<211> LENGTH: 22
<212> TYPE: DNA
<213> ORGANISM: Homo sapiens

<400> SEQUENCE: 9
gataagcaag gagaaaggtg at                                           22

<210> SEQ ID NO 10
<211> LENGTH: 20
<212> TYPE: DNA
<213> ORGANISM: Homo sapiens

<400> SEQUENCE: 10
ctcttagagt ttcttggacc                                              20

<210> SEQ ID NO 11
<211> LENGTH: 21
<212> TYPE: DNA
<213> ORGANISM: Homo sapiens

<400> SEQUENCE: 11
ccagaagtac aagcagtctg g                                            21

<210> SEQ ID NO 12
<211> LENGTH: 20
<212> TYPE: DNA
```

<213> ORGANISM: Homo sapiens

<400> SEQUENCE: 12 tctgcttttta tagttcaagg                                              20

<210> SEQ ID NO 13
<211> LENGTH: 22
<212> TYPE: DNA
<213> ORGANISM: Homo sapiens

<400> SEQUENCE: 13
ggatccttca ataacttca gg                                             22

<210> SEQ ID NO 14
<211> LENGTH: 20
<212> TYPE: DNA
<213> ORGANISM: Homo sapiens

<400> SEQUENCE: 14
cttctacaga tgataacacc                                               20

<210> SEQ ID NO 15
<211> LENGTH: 16
<212> TYPE: DNA
<213> ORGANISM: Homo sapiens

<400> SEQUENCE: 15
gaagctccat aatggg                                                   16

<210> SEQ ID NO 16
<211> LENGTH: 2243
<212> TYPE: DNA
<213> ORGANISM: Homo sapiens

<400> SEQUENCE: 16

| | | | | | |
|---|---|---|---|---|---|
| ggacgtcgag | gcattacaat | cgcgaaacca | agccatagca | tgaaacagcg | agcttgcagc | 60 |
| ctcaccgacg | agtctcaact | aaaagggact | cccggagcta | ggggtgggga | ctcggcctca | 120 |
| cacagtgagt | gccggctatt | ggacttttgt | ccagtgacag | ctgagacaac | aaggaccacg | 180 |
| ggaggaggtg | taggagagaa | gcgccgcgaa | cagcgatcgc | ccagcaccaa | gtccgcttcc | 240 |
| aggctttcgg | tttctttgcc | tccatctttgg | gtgcgccttc | ccggcgtcta | ggggagcgaa | 300 |
| ggctgaggtg | gcagcggcag | gagagtccgg | ccgcgacagg | acgaactccc | ccactggaaa | 360 |
| ggattctgaa | agaaatgaag | tcagccctca | gaaatgaagt | tgactgcctg | ctggcttttcc | 420 |
| tgttgactgg | cccggagctg | tactgcaaga | cccttgtgag | cttccctagt | ctaagagtag | 480 |
| gatgtctgct | gaagtcatcc | atcaggttga | agaagcactt | gatacagatg | agaaggagat | 540 |
| gctgctcttt | ttgtgccggg | atgttgctat | agatgtggtt | ccacctaatg | tcagggacct | 600 |
| tctggatatt | ttacgggaaa | gaggtaagct | gtctgtcggg | gacttggctg | aactgctcta | 660 |
| cagagtgagg | cgatttgacc | tgctcaaacg | tatcttgaag | atggacagaa | aagctgtgga | 720 |
| gacccacctg | ctcaggaacc | ctcaccttgt | ttcggactat | agagtgctga | tgcagagatt | 780 |
| tggtgaggat | ttggataaat | ctgatgtgtc | ctcattaatt | ttcctcatga | aggattacat | 840 |
| gggccgaggc | aagataagca | aggagaagag | tttcttggac | cttgtggttg | agttggagaa | 900 |
| actaaatttg | gttgccccag | atcaactgga | tttattagaa | aaatgcctaa | agaacatcca | 960 |
| cagaatagac | ctgaagacaa | aaatccagaa | gtacaagcag | tctgttcaag | gagcagggac | 1020 |
| aagttacagg | aatgttctcc | aagcagcaat | ccaaaagagt | ctcaaggatc | cttcaaataa | 1080 |

```
cttcaggctc cataatggga gaagtaaaga acaaagactt aaggaacagc ttggcgctca    1140
acaagaacca gtgaagaaat ccattcagga atcagaagct tttttgcctc agagcatacc    1200
tgaagagaga tacaagatga agagcaagcc cctaggaatc tgcctgataa tcgattgcat    1260
tggcaatgag acagagcttc ttcgagacac cttcacttcc ctgggctatg aagtccagaa    1320
attcttgcat ctcagtatgc atggtatatc ccagattctt ggccaatttg cctgtatgcc    1380
cgagcaccga gactacgaca gctttgtgtg tgtcctggtg agccgaggag gctcccagag    1440
tgtgtatggt gtggatcaga ctcactcagg gctcccctg catcacatca ggaggatgtt    1500
catgggagat tcatgccctt atctagcagg gaagccaaag atgttttta ttcagaacta    1560 tgtggtgtca gagggccagc tggagaacag cagcctcttg gaggtggatg ggccagcgat    1620
gaagaatgtg gaattcaagg ctcagaagcg agggctgtgc acagttcacc gagaagctga    1680
cttcttctgg agcctgtgta ctgcggacat gtccctgctg gagcagtctc acagctcacc    1740
gtccctgtac ctgcagtgcc tctcccagaa actgagacaa gaaagaaaac gcccactcct    1800
ggatcttcac attgaactca atggctacat gtatgattgg aacagcagag tttctgccaa    1860
ggagaaatat tatgtctggc tgcagcacac tctgagaaag aaacttatcc tctcctacac    1920
ataagaaacc aaaaggctgg gcgtagtggc tcacacctgt aatcccagca ctttgggagg    1980
ccaaggaggg cagatcactt caggtcagga gttcgagacc agcctggcca acatggtaaa    2040
cgctgtccct agtaaaaatg caaaaattag ctgggtgtgg gtgtgggtac ctgtgttccc    2100
agttacttgg gaggctgagg tgggaggatc ttttgaaccc aggagttcag ggtcatagca    2160
tgctgtgatt gtgcctacga atagccactg cataccaacc tgggcaatat agcaagatcc    2220
catctcttta aaaaaaaaa aaa                                             2243

<210> SEQ ID NO 17
<211> LENGTH: 20
<212> TYPE: DNA
<213> ORGANISM: Artificial Sequence
<220> FEATURE:
<223> OTHER INFORMATION: Antisense sequence to region spanning the AUG
      start site of cFLIP

<400> SEQUENCE: 17
cttcagcaga catcctactc                                                  20

<210> SEQ ID NO 18
<211> LENGTH: 20
<212> TYPE: DNA
<213> ORGANISM: Artificial Sequence
<220> FEATURE:
<223> OTHER INFORMATION: Antisense sequence to region 5' of start site
      of cFLIP

<400> SEQUENCE: 18
gactagggaa gctcacaagg                                                  20

<210> SEQ ID NO 19
<211> LENGTH: 20
<212> TYPE: DNA
<213> ORGANISM: Artificial Sequence
<220> FEATURE:
<223> OTHER INFORMATION: Antisense region to site to region 3' of start
      site of cFLIP

<400> SEQUENCE: 19
tcaacctgat ggatgacttg                                                  20
```

-continued

```
<210> SEQ ID NO 20
<211> LENGTH: 19
<212> TYPE: DNA
<213> ORGANISM: Artificial Sequence
<220> FEATURE:
<223> OTHER INFORMATION: Antisense sequence to Exon 4 splice donor site
      of cFLIP

<400> SEQUENCE: 20
cctatagtcc gaaacaagg                                                   19

<210> SEQ ID NO 21
<211> LENGTH: 19
<212> TYPE: DNA
<213> ORGANISM: Artificial Sequence
<220> FEATURE:
<223> OTHER INFORMATION: Antisense sequence to Exon 5 splice acceptor
      site of cFLIP

<400> SEQUENCE: 21
catcagcact ctgcaaacc                                                   19

<210> SEQ ID NO 22
<211> LENGTH: 22
<212> TYPE: DNA
<213> ORGANISM: Artificial Sequence
<220> FEATURE:
<223> OTHER INFORMATION: Antisense sequence to Exon 5 splice donor site
      of cFLIP

<400> SEQUENCE: 22
ctcacctttc tccttgctta tc                                               22

<210> SEQ ID NO 23
<211> LENGTH: 20
<212> TYPE: DNA
<213> ORGANISM: Artificial Sequence
<220> FEATURE:
<223> OTHER INFORMATION: Antisense sequence to Exon 6 splice acceptor
      site of cFLIP

<400> SEQUENCE: 23
ggtccaagaa actctaagag                                                  20

<210> SEQ ID NO 24
<211> LENGTH: 21
<212> TYPE: DNA
<213> ORGANISM: Artificial Sequence
<220> FEATURE:
<223> OTHER INFORMATION: Antisense sequence to Exon 6 splice donor site
      of cFLIP

<400> SEQUENCE: 24
ccagactgct tgtacttctg g                                                21

<210> SEQ ID NO 25
<211> LENGTH: 20
<212> TYPE: DNA
<213> ORGANISM: Artificial Sequence
<220> FEATURE:
<223> OTHER INFORMATION: Antisense sequence to Exon 7 splice acceptor
      site of cFLIP

<400> SEQUENCE: 25
ccttgaacta taaaagcaga                                                  20

<210> SEQ ID NO 26
<211> LENGTH: 22
```

```
<212> TYPE: DNA
<213> ORGANISM: Artificial Sequence
<220> FEATURE:
<223> OTHER INFORMATION: Antisense sequence to Exon 7 splice donor site
      of cFLIP

<400> SEQUENCE: 26
cctgaagtta tttgaaggat cc                                              22

<210> SEQ ID NO 27
<211> LENGTH: 20
<212> TYPE: DNA
<213> ORGANISM: Artificial Sequence
<220> FEATURE:
<223> OTHER INFORMATION: Antisense sequence to Exon 8 splice acceptor
      site of cFLIP

<400> SEQUENCE: 27
ggtgttatca tctgtagaag                                                 20

<210> SEQ ID NO 28
<211> LENGTH: 16
<212> TYPE: DNA
<213> ORGANISM: Artificial Sequence
<220> FEATURE:
<223> OTHER INFORMATION: Antisense sequence to Exon 9 splice acceptor
      site of cFLIP

<400> SEQUENCE: 28
cccattatgg agcttc                                                     16

<210> SEQ ID NO 29
<211> LENGTH: 19
<212> TYPE: DNA
<213> ORGANISM: Artificial Sequence
<220> FEATURE:
<223> OTHER INFORMATION: Antisense sequence to cFLIP start site sequence
<220> FEATURE:
<221> NAME/KEY: Misc
<222> LOCATION: (1)..(1)
<223> OTHER INFORMATION: conjugated to SEQ ID NO:1

<400> SEQUENCE: 29
ctgggccatg ttcagaacc                                                  19

<210> SEQ ID NO 30
<211> LENGTH: 19
<212> TYPE: DNA
<213> ORGANISM: Artificial Sequence
<220> FEATURE:
<223> OTHER INFORMATION: Antisense sequence to cFLIP start site sequence
<220> FEATURE:
<221> NAME/KEY: MIsc
<222> LOCATION: (1)..(1)
<223> OTHER INFORMATION: conjugated to SEQ ID NO:2

<400> SEQUENCE: 30
ctgggccatg ttcagaacc                                                  19

<210> SEQ ID NO 31
<211> LENGTH: 19
<212> TYPE: DNA
<213> ORGANISM: Artificial Sequence
<220> FEATURE:
<223> OTHER INFORMATION: rTAT scrambled antisense sequence

<400> SEQUENCE: 31
cgtgcgctat gtgacacac                                                  19
```

US 8,008,469 B2

ANTISENSE COMPOUND FOR INDUCING IMMUNOLOGICAL TOLERANCE

This application claims priority to U.S. patent application Ser. No. 10/946,881, filed Sep. 22, 2004, which claims the benefit of U.S. Provisional Application No. 60/505,418 filed Sep. 23, 2003, which are both hereby incorporated by reference in their entirety.

FIELD OF THE INVENTION

The present invention relates to compounds and methods of inducing immunological tolerance using a peptide-antisense conjugate to selectively eliminate activated immune cells, e.g., activated T-cells.

REFERENCES

The following references are cited as part of the background of the invention or to support certain methods or procedures in the invention.

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Akhtar, S., S. Basu, et al. (1991). "Interactions of antisense DNA oligonucleotide analogs with phospholipid membranes (liposomes)." *Nucleic Acids Res* 19(20): 5551-9.

Anderson, C. M., W. Xiong, et al. (1999). "Distribution of equilibrative, nitrobenzylthioinosine-sensitive nucleoside transporters (ENT1) in brain." *J Neurochem* 73(2): 867-73.

Anderson, K. P., M. C. Fox, et al. (1996). "Inhibition of human cytomegalovirus immediate-early gene expression by an antisense oligonucleotide complementary to immediate-early RNA." *Antimicrob Agents Chemother* 40(9): 2004-11.

Bonham, M. A., S. Brown, et al. (1995). "An assessment of the antisense properties of RNase H-competent and steric-blocking oligomers." *Nucleic Acids Res* 23(7):1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 292531.

Ding, D., S. M. Grayaznov, et al. (1996). "An oligodeoxyribonucleotide N3'-->P5' phosphoramidate duplex forms an A-type helix in solution." *Nucleic Acids Res* 24(2): 354-60.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Gupta, S. (2003). "Molecular signaling in death receptor and mitochondrial pathways of apoptosis (Review)." *Int J Oncol* 22(1):15-20.

Hudziak, R. M., E. Barofsky, et al. (1996). "Resistance of morpholino phosphorodiamidate oligomers to enzymatic degradation." *Antisense Nucleic Acid Drug Dev* 6(4): 267-72.

Loke, S. L., C. A. Stein, et al. (1989). "Characterization of oligonucleotide transport into living cells." *Proc Natl Acad Sci USA* 86(10): 3474-8.

Moulton, H. M., M. C. Hase, et al. (2003). "HIV Tat peptide enhances cellular delivery of antisense morpholino oligomers." *Antisense Nucleic Acid Drua Dev* 13(1): 31-43.

Moulton, H. M. and J. D. Moulton (2003). "Peptide-assisted delivery of steric-blocking antisense oligomers." *Curr Opin Mol Ther* 5(2): 123-32.

Murphy, K. M., A. B. Heimberger, et al. (1990). "Induction by antigen of intrathymic apoptosis of CD4+CD8+TCRIo thymocytes in vivo." *Science* 250(4988): 1720-3.

Pari, G. S., A. K. Field, et al. (1995). "Potent antiviral activity of an antisense oligonucleotide complementary to the intron-exon boundary of human cytomegalovirus genes UL36 and UL37." *Antimicrob Agents Chemother* 39(5): 1157-61.

Stein, D., E. Foster, et al. (1997). "A specificity comparison of four antisense types: morpholino, 2'-O-methyl RNA, DNA, and phosphorothioate DNA." *Antisense Nucleic Acid Drug Dev* 7(3): 151-7.

Summerton, J. and D. Weller (1997). "Morpholino antisense oligomers: design, preparation, and properties." *Antisense Nucleic Acid Drug Dev* 7(3): 187-95.

Toulme, J. J., R. L. Tinevez, et al. (1996). "Targeting RNA structures by antisense oligonucleotides." *Biochimie* 78(7): 663-73.

Wasem, C., D. Arnold, et al. (2003). "Sensitizing antigen-specific CD8+T cells for accelerated suicide causes immune incompetence." *J Clin Invest* 111(8): 1191-9.

Vanin, E. F. and Ji, T. H., *Biochemistry* 20:6754-6760 (1981).

Wender, P. A., D. J. Mitchell, et al. (2000). "The design, synthesis, and evaluation of molecules that enable or enhance cellular uptake: peptoid molecular transporters." *Proc Natl Acad Sci USA* 97(24): 13003-8.

Yakubov, L. A., E. A. Deeva, et a!. (1989). "Mechanism of oligonucleotide uptake by cells: involvement of specific receptors?" *Proc Natl Acad Sci USA* 86(17): 6454-8

BACKGROUND OF THE INVENTION

Transplantation of allogeneic donor cells, tissues or organs (transplantation between genetically different individuals of the same species) is used to treat a variety of conditions—typically tissue- or organ-failure conditions—and is often the sole or highly preferred therapeutic option. The list of successfully transplanted cells, tissues and organs includes kidney, heart, lung, liver, corneas, pancreas, marrow, skin, and bones. However, allogeneic transplantation involves significant risks and drawbacks, including graft rejection, complications from immunosuppressive therapy and graft-versus host disease which are frequently highly debilitating or lethal.

Rejection of allografts is presently understood to be initiated by the recognition of allogeneic (i.e. donor) major histocompatibility complex (MHC) molecules by recipient T-lymphocytes, leading to upregulated cellular and humoral immunity through activation of T cells. The MHC antigens are typically presented to the recipient T-lymphocytes by antigen presenting cells, such as macrophages and dendritic cells. Although immunosuppressive drugs such as cyclosporine may be used in an attempt to modulate rejection, these immunosuppressive agents have severe side effects and often fail to prevent continued rejection episodes.

Activated T cells also play a critical role in autoimmune disorders. Immunologic tolerance to self antigens is a necessary mechanism for protecting an organism from destruction by its own immune system. When this mechanism malfunctions, allowing self-reactive immune cells, including activated T cells, to proliferate, an autoimmune disease may develop within the host. A number of diseases such as multiple sclerosis, lupis, myathenia gravis, inflammatory bowel disease and rheumatoid arthritis, have been shown to result from loss of self-tolerance in T and B lymphocytes.

There is thus a need for therapeutic methods and compositions capable of inducing immunological tolerance with lower toxicity and improved efficacy.

SUMMARY OF THE INVENTION

In one aspect, the invention is directed to a method of achieving selective uptake of a substantially uncharged antisense compound into antigen-activated T cells. In the method, a population of mammalian T cells that include antigen-activated and non-activated T cells are exposed to an rTAT-antisense conjugate composed of (i) the antisense compound and (ii) covalently coupled thereto, a reverse TAT (rTAT) polypeptide having the sequence identified as SEQ ID NO:1. The exposing step is effective to achieve a greater level of intracellular uptake of the antisense compound into antigen-activated T cells than is achieved (i) by exposing non-activated T cells to the same rTAT-antisense conjugate, or (ii) by exposing antigen-activated T cells to the antisense compound in the absence of the rTAT polypeptide.

The antisense compound in the conjugate to which the T cells are exposed may be composed of morpholino subunits and phosphorus-containing intersubunit linkages joining a morpholino nitrogen of one subunit to a 5' exocyclic carbon of an adjacent subunit. The morpholino subunits in the conjugate may be joined by phosphorodiamidate linkages, in accordance with the structure:

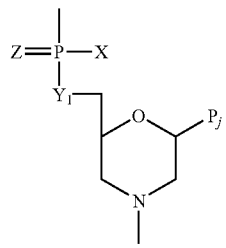

where $Y_1$=O, Z=O, PJ is a purine or pyrimidine base-pairing moiety effective to bind, by base-specific hydrogen bonding, to a base in a polynucleotide, and X is alkyl, alkoxy, thioalkoxy, amino or alkyl amino, e.g., where X=$NR_2$, where each R is independently hydrogen or methyl.

In a more general aspect, the invention includes selectively enhancing the uptake of a substantially uncharged therapeutic compound into activated immune cells, such as antigen-activated T cells, B cells, or mature dendritic cells, by coupling the compound to a reverse TAT (rTAT) polypeptide. In one embodiment, the therapeutic compound is a substantially uncharged oligonucleotide analog. The linkage between the rTAT polypeptide and therapeutic compound may be a biodegradable linkage, such as an ester, peptide or disulfide linkage.

In another aspect, the invention includes a method of selectively killing activated T cells. In practicing the method, a population of mammalian T cells that include antigen-activated and non-activated T cells are exposed to an rTAT-antisense conjugate compound composed of (i) a substantially uncharged antisense compound containing 12-40 subunits and a base sequence effective to hybridize to a region of preprocessed or processed human cFLIP transcript identified, in its processed form, by SEQ ID NO:16, thereby to block expression of CFLIP in T cells, and (ii) an rTAT polypeptide having the sequence identified as SEQ ID NO: 1 and covalently coupled to the antisense compound. The exposing step results in selective uptake of the antisense conjugate into antigen-activated T cells, relative to the uptake of the conjugate into non-activated T cells in the population, promoting antigen activated cell death selectively in the antigen-activated T cells.

The antisense compound may have the exemplary structural features noted above, and the rTAT polypeptide in the conjugate may be covalently coupled at its N-terminal cysteine residue to the 3' or 5' end of the antisense compound.

In one general embodiment designed to target the start site of the processed human cFLIP transcript, the antisense compound has a base sequence that is complementary to a target region containing at least 12 contiguous bases in a processed human cFLIP transcript, and which includes at least 6 contiguous bases of one of the sequences identified by SEQ ID NOS:4-6. Exemplary antisense sequences include those identified as SEQ ID NOS:17-19.

In another general embodiment designed to target a splice site of preprocessed human cFLIP, the antisense compound has a base sequence that is complementary to a target region containing at least 12 contiguous bases in a preprocessed human cFLIP transcript, and which includes at least 6 contiguous bases of one of the sequences identified by SEQ ID NOS:7-15. Exemplary antisense sequences include those identified as SEQ ID NOS:20-28.

Where the method is used for inhibiting transplantation rejection in a human subject receiving an allograft tissue or organ, the exposing step involves administering the antisense conjugate to the subject in an amount effective to inhibit the rate and extent of rejection of the transplant. The administering may be carried out both prior to and following the allograft tissue or organ transplantation in the subject.

Where the method is used for use in treating an autoimmune condition in a human subject, the exposing step involves administering the antisense conjugate to the subject, in an amount effective to reduce the severity of the autoimmune condition.

In a more general aspect, the invention provides a method of enhancing uptake of a substantially uncharged antisense compound selectively into antigen-activated mammalian T cells, antigen-activated B cells, or mature dendritic cells, by covalently attaching the oligonucleotide compound, an rTAT polypeptide having the polypeptide sequence identified as SEQ ID NO: 1.

In one exemplary embodiment, the rTAT polypeptide is covalently coupled at its N-terminal cysteine residue to the 3' or 5' end of the antisense compound. Also in an exemplary embodiment, the antisense compound is composed of morpholino subunits and phosphorus-containing intersubunit linkages joining a morpholino nitrogen of one subunit to a 5' exocyclic carbon of an adjacent subunit.

The invention further includes an antisense conjugate for use in selectively targeting antigen-activated mammalian T cells, antigen-activated B cells, or mature dendritic cells with an antisense compound. The compound is composed of (i) a substantially uncharged antisense compound containing 12-40 subunits and a base sequence effective to hybridize to a region of preprocessed or processed human cFLIP transcript identified, in its processed form, by SEQ ID NO:16, thereby to block expression of cFLIP in T cells, and (ii) a reverse TAT (rTAT) polypeptide having the sequence identified as SEQ ID NO: 1 and covalently coupled to the antisense compound. The compound may have various exemplary structural features, as described above.

Also disclosed is a method for treating transplantation rejection or an autoimmune condition in a subject. The method includes administering to the subject, a substantially uncharged antisense compound containing 12-40 subunits and a base sequence effective to hybridize to a region of preprocessed or processed human cFLIP transcript identified by SEQ ID:16, and by said hybridizing, to block expression of cFLIP in T cells.

The compound may be composed of phosphorus-containing intersubunit linkages joining a morpholino nitrogen of one subunit to a 5' exocyclic carbon of an adjacent subunit. The morpholino subunits in the compound may be joined by phosphorodiamidate linkages, in accordance with the structure:

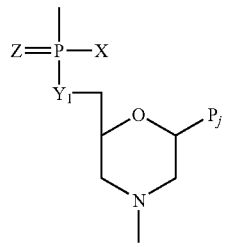

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, e.g., where X=$NR_2$, where each R is independently hydrogen or methyl.

Where the antisense compound administered is effective to target the start site of the processed human cFLIP transcript, it may have a base sequence complementary to a target region containing at least 12 contiguous bases in a processed human cFLIP transcript, and which includes at least 6 contiguous bases of one of the sequences identified by SEQ ID NOS:4-6. Exemplary antisense sequences include those identified as SEQ ID NOS:17-19.

Where the antisense compound administered is effective to target a splice site of preprocessed human cFLIP, it may have a base sequence complementary to a target region containing at least 12 contiguous bases in a preprocessed human cFLIP transcript, and which includes at least 6 contiguous bases of one of the sequences identified by SEQ ID NOS:7-15. Exemplary antisense sequences include those identified by SEQ ID NOS:20-28.

These and other objects and features of the invention will become more fully apparent when the following detailed description of the invention is read in conjunction with the accompanying drawings.

BRIEF DESCRIPTION OF THE DRAWINGS

FIGS. 6A-6C show FACS analysis of antigen-specific AICD in ovalbumin-specific T cells when treated with cFLIP-PMO. In FIG. 6A, fluorescence is due to caspase-3 activity in activated and non-activated T cells. In FIGS. 6B and 6C, fluorescence is due to propidium iodide staining (as a measure of apoptosis) in PMO-treated and untreated cells, with and without activation.

DETAILED DESCRIPTION OF THE INVENTION

I. Definitions

Figure 1A:
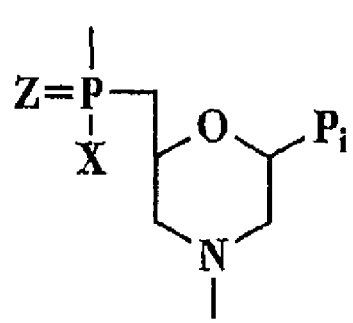
FIG. 1A-D show several preferred morpholino-type subunits having 5-atom (A), six-atom (B) and seven-atom (C-D) linking groups suitable for forming polymers.

The terms below, as used herein, have the following meanings, unless indicated otherwise.

The term "antigen-activated T cells" refers to T cells that become activated after the T cell receptor (TCR) complex and a co-stimulatory receptor (e.g. CD28 on naive CD4 and CD8 T cells) are engaged to the extent that a signal transduction cascade is initiated. Antigen is bound by the TCR in the form of a foreign peptide in the context of a self MHC molecule, either Class I or Class II, in the case of CD4 and CD8 T cells respectively, conferring the antigen specificity of the T cell. Upon activation, T cells will proliferate and then secrete cytokines or carry out cytolysis on cells expressing the foreign peptide with self MHC. Cytokines are growth factors for other T cells or signals for B cells to produce antibody.

The term "antigen-activated B cells" refer to either of two different types of B cell activation, T cell dependent and T cell independent. T cell independent antigens contain repetitive identical epitopes and are capable of clustering membrane bound antibody on the surface of the B cell which can result in delivering activation signals. T cell dependent activation is in response to protein antigens where the B cell acts as a professional antigen presenting cell. Surface antibody bound to antigen is internalized by the B cell, the antigen processed and presented as peptides on the B cell surface bound to MHC II molecules. Responding T cells recognize the peptide as foreign in the context of self MHC and respond by secreting cytokines and expression of CD40L. Together these provide a co-stimulatory signal to the B cell. In either case of B cell activation the cell will proliferate and differentiate into plasma B cells capable of secreting antibodies against the antigen.

The term "mature dendritic cells" (DCs) refer to professional antigen-presenting cells (APCs) capable of expressing both MHC class I and II and co-stimulatory molecules. Two different DC phenotypes are exhibited depending on maturation state and location in the body. Immature DCs reside in all tissues and organs as active phagocytic cells. Mature DCs traffic to secondary lymphoid organs (e.g. lymph node and spleen) and present peptides derived from processed protein antigens to T cells in the context of MHC molecules. Mature DCs also provide the necessary co-stimulatory signals to T cells by expressing the appropriate surface ligand (e.g. CD80 and CD86 on DCs bind to CD28 on T cells)

The terms "antisense oligonucleotides," "antisense oligomer," and "antisense compound" are used interchangeably and refer to a compound having sequence of nucleotide bases and a subunit-to-subunit backbone that allows the antisense oligomer to hybridize to a target sequence in an RNA by Watson-Crick base pairing, to form an RNA: oligomer heteroduplex within the target sequence. The antisense oligonucleotide includes a sequence of purine and pyrimidine heterocyclic bases, supported by a backbone, which are effective to hydrogen-bond to corresponding, contiguous bases in a target nucleic acid sequence. The backbone is composed of subunit backbone moieties supporting the purine and pyrimidine heterocyclic bases at positions that allow such hydrogen bonding. These backbone moieties are cyclic moieties of 5 to 7 atoms in length, linked together by phosphorous-containing linkages one to three atoms long.

A "morpholino" oligonucleotide refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIGS. 9A-9E, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. Exemplary structures for antisense oligonucleotides for use in the invention include the morpholino subunit types shown in FIGS. 1A-1D, with the uncharged, phosphorous-containing linkages shown in FIGS. 2A-2D, and more generally, the uncharged linkages 3A-3G.

As used herein, an oligonucleotide or antisense oligomer "specifically hybridizes" to a target polynucleotide if the oligomer hybridizes to the target under physiological conditions, with a thermal melting point (Tm) substantially greater than 37° C., preferably at least 45° C., and typically 50° C. -80° C. or higher. Such hybridization preferably corresponds to stringent hybridization conditions, selected to be about 10° C. , and preferably about 50° C. lower than the Tm for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein the term "analog" with reference to an oligomer means a substance possessing both structural and chemical properties similar to those of the reference oligomer.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, "effective amount" relative to an antisense oligomer refers to the amount of antisense oligomer administered to a subject, either as a single dose or as part of a series of doses, that is effective to inhibit expression of a selected target nucleic acid sequence.

Abbreviations:
PMO=morpholino oligomer
AICD=activation induced cell death
FLICE=FADD-like IL-1-beta-converting enzyme, aka, protease caspase-8.
cFLIP=cellular FLICE inhibitory protein II. The role of activated T cells in transplantation and autoimmune disorders Programmed cell death (a.k.a. apoptosis) is a key feature of many biological processes including the regulation and resolution of immune responses and immunological tolerance. Specifically, apoptosis plays a critical role in maintaining immune homeostasis and peripheral tolerance to self-antigens through the deletion of self-reactive lymphocytes by activation induced cell death (AICD).

One of the early initiator proteins of apoptosis in many cell types including B, T and dendritic cells is the protease caspase-8 (a.k.a. FLICE or FADD-like IL-1-beta-converting enzyme) (Gupta 2003). T cells are particularly susceptible to apoptosis during the early stages of antigen recognition due to the activation of FLICE. In the absence of appropriate co-stimulatory signals, self-reactive T cells are unable to express a cellular FLICE inhibitory protein (CFLIP) and succumb to AICD. Conversely, T cells responding to a pathogen, for example, would receive co-stimulatory signals, express cFLIP and thus proliferate and differentiate into effector cells mediating either antibody production or cytolysis.

The major histocompatibility (MHC) antigen differences are the primary way a transplant is seen as non-self and thus T cells respond mainly with activated CD8 T cells destroying the tissue by cytolysis (release of perforin and granule particles containing enzymes that induce cells under attack to undergo apoptosis). Allotypic CD8 T cell responses are directed to small differences in protein sequences of the donor tissues. When these are processed and presented in the context of either the donor's matched MHC class I molecules or when acquired by the host APCs, CD8 T cells can be activated and thus reject tissue. However, this may only be a minor portion of the CD8 and CD4 T cells responses produced against a miss matched transplant.

A critical component of T cell ontogeny is Central Tolerance. During initial stages of T cell development, which occurs in the thymus, the T cells undergo two important selection processes. The first is positive selection. If the TCR made by a particular T cell clone does not have the ability to bind MHC then these T cells die. Thus what remains are T cells capable of recognizing the presence of self (MHC on a cell) and can respond if a peptide is presented by that MHC molecule binds to the TCR. The second process is when the cells undergo negative selection. In this stage the T cells that bind to self MHC too tightly receive a signal to die. T cells may bind too tightly for two reasons; 1) A processed peptide from a self protein is being presented and the TCR recognizes that peptide in the context of MHC or; 2) The TCR binds to the MHC tightly regardless of the peptide being presented. It is the context of self recognition (general recognition) and not the peptide (discrete recognition) that signals these T cells to die. What remains are a repertoire of T cell clones that can recognize if a cell is contextually self (correct MHC) and respond if there is altered-self (i.e. a peptide not present during negative selection).

For a successful transplant to occur the match between donor and recipient MHCs is crucial because of Central Tolerance. The recipient's T cells never had the "benefit" of undergoing the negative selection process with the donors MHC present. Therefore, independent of the peptides the donor tissues might be presenting, if T cells bind to the MHC tightly then they will be come activated and carry out a response. This allotypic response will occur if the MHCs are not exactly matched and these make up the majority of the responding T cells responsible for rejection regardless of their peptide specificity. Since all of the cells in the transplant will express the miss-matched MHC they are subjected to recognition and attack. The same process holds true for CD4 T cells but they would only recognize class II molecules on professional APCs (MACS, DCs and B cells). This would result in a large production of cytokines and possibly allo-specific antibodies.

Defects in the AICD process such as the constitutive expression of cFLIP can result in the expansion of self-reactive effector T cells and ultimately autoimmune disease (Wasem, Arnold et al. 2003). In a variety of autoimmune diseases, T cells respond to self antigens the way they normally would toward any non-self peptide. Reasons vary including faulty negative selection against self-peptides, dysfunctional peripheral tolerance, altered proteins in normal tissues or molecular mimicry where a pathogen with a similar antigen activates the immune response sufficiently to cause T cells to respond to a protein similar to self. In general little is known about what causes the initial T cell activation. However, if some potentially self-reactive T cells can bypass both central and peripheral tolerance mechanisms, either of these due to constitutive expression of cFLIP, these cells would proliferate and cause tissue destruction. Blocking their ability to survive by blocking cFLIP expression could help in reducing the population of self-reactive T cells and the severity of the autoimmune condition.

III. rTAT-Antisense Conjugate for Targeting Activated Immune Cells

The present invention is based, in part, on the discovery that the uptake of uncharged of substantially uncharged antisense compounds into activated human immune cells, such as activated mammalian T cells, antigen-activated B cells, or mature dendritic cells, can be selectively enhanced, with respect to non-activated immune cells, by conjugating the antisense compound with an rTAT polypeptide. This section describes various exemplary antisense compounds, the rTAT polypeptide, and methods of producing the rTAT-antisense conjugate.

A. Antisense Compound

Antisense oligomers for use in practicing the invention, preferably have the properties: (1) a backbone that is substantially uncharged, (2) the ability to hybridize with the complementary sequence of a target RNA with high affinity, that is a Tm substantially greater than 37° C., preferably at least 45° C., and typically greater than 50° C., e.g., 60° C.-80° C. or higher, (3) a subunit length of at least 8 bases, generally about 8-40 bases, preferably 12-25 bases, and (4) nuclease resistance (Hudziak, Barofsky et al. 1996).

In addition, the antisense compound may have the capability for active or facilitated transport as evidenced by (i) competitive binding with a phosphorothioate antisense oligomer, and/or (ii) the ability to transport a detectable reporter into target cells. In particular, for purposes of transport, the antisense compound displays selective uptake into activated immune cells when conjugated with rTAT polypeptide, according to cell-uptake criteria set out below.

Candidate antisense oligomers may be evaluated, according to well known methods, for acute and chronic cellular toxicity, such as the effect on protein and DNA synthesis as measured via incorporation of 3H-leucine and 3H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests is important in discerning specific effects of antisense inhibition of gene expression from indiscriminate suppression. Accordingly, sequences may be modified as needed to limit non-specific binding of antisense oligomers to non-target nucleic acid sequences.

Heteroduplex formation. The effectiveness of a given antisense oligomer molecule in forming a heteroduplex with the target mRNA may be determined by screening methods known in the art. For example, the oligomer is incubated in a cell culture containing an mRNA preferentially expressed in activated lymphocytes, and the effect on the target mRNA is evaluated by monitoring the presence or absence of (1) heteroduplex formation with the target sequence and non-target sequences using procedures known to those of skill in the art, (2) the amount of the target mRNA expressed by activated lymphocytes, as determined by standard techniques such as RT-PCR or Northern blot, (3) the amount of protein transcribed from the target mRNA, as determined by standard techniques such as ELISA or Western blotting. (See, for example,(Pari, Field et al. 1995; Anderson, Fox et al. 1996).

For the purposes of the invention, a preferred test for the effectiveness of the cFLIP antisense oligomer is by measuring the induction of apoptosis due to AICD. Splenocytes from DO11.10 mice containing naive lymphocytes are treated with cFLIP PMO prior to co-culture with antigen (ovalbumin) presenting dendritic cells. Apoptosis, i.e. activation of caspase-3, is detected by propidium iodide staining only when the cFLIP PMO has effectively reduced cFLIP expression.

Uptake into cells. A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy or FACS analysis, for intracellular label. The presence of significant intracellular label is evidence that the test compound is transported by facilitated or active transport.

In one aspect of the invention, uptake into cells is enhanced by administering the antisense compound in combination with an arginine-rich peptide linked to the 5' or 3' end of the antisense oligomer. The peptide is typically 8-16 amino acids and consists of a mixture of arginine, and other amino acids including phenylalanine and cysteine. Exemplary arginine rich peptides are disclosed (SEQ ID NOS:1-3). As will be seen below, the rTAT polypeptide identified by SEQ ID NO: 1 allows for selective uptake by activated immune cells, so is chosen in those methods for which selective uptake into activated immune cells is important.

RNAse resistance. Two general mechanisms have been proposed to account for inhibition of expression by antisense oligonucleotides (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer: RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing, translation, or replication. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test otigomer can be assayed for its RNaseH resistance by forming an RNA: oligomer duplex with the test compound, then incubating the duplex with RNaseH under a standard assay conditions, as described (Stein, Foster et al. 1997). After exposure to RNaseH, the presence or absence of intact duplex can be monitored by gel electrophoresis or mass spectrometry.

In vivo uptake. In accordance with another aspect of the invention, there is provided a simple, rapid test for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. Pat. No. 6,365,351 for "Non-Invasive Method for Detecting Target RNA," the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including RNA encoded by a host gene. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

Structural features. As detailed above, the antisense oligomer has a base sequence directed to a targeted portion of a cellular gene, preferably the region surrounding the start codon or splice sequence of the cFLIP mRNA or preprocessed transcript. In addition, the oligomer is able to effectively inhibit expression of the targeted gene when administered to a host cell, e.g. in a mammalian subject. This requirement is met when the oligomer compound (a) has the ability to be selectively taken up by activated T cells (or other activated immune cells) and (b) once taken up, form a duplex with the target RNA with a Tm greater than about 45° C.

The ability to be taken up selectively by activated immune cells requires, in part, that the oligomer backbone be substantially uncharged. The ability of the oligomer to form a stable duplex with the target RNA will depend on the oligomer backbone, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Antisense oligonucleotides of 15-20 bases are generally long enough to have one complementary sequence in the mammalian genome. In addition, antisense compounds having a length of at least 17 nucleotides in length hybridize well with their target mRNA(Akhtar, Basu et al. 1991). Due to their hydrophobicity, antisense oligonucleotides interact well with phospholipid membranes (Akhtar, Basu et al. 1991), and it has been suggested that following the interaction with the cellular plasma membrane, oligonucleotides are actively transported into living cells (Loke, Stein et al. 1989; Yakubov, Deeva et al. 1989; Anderson, Xiong et al. 1999).

Morpholino oligonucleotides, particularly phosphoramidate- or phosphorodiamidate-linked morpholino oligonucleotides have been shown to have high binding affinities for complementary or near-complementary nucleic acids. Morpholino oligomers also exhibit little or no non-specific antisense activity, afford good water solubility, are immune to nucleases, and are designed to have low production costs (Summerton and Weller 1997).

Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein In one preferred approach, antisense oligomers for use in practicing the invention are composed of morpholino subunits of the form shown in the above cited patents, where (i) the morpholino groups are linked together by uncharged linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton et al., 1993), which is hereby incorporated by reference in its entirety. As shown in this reference, several types of nonionic linkages may be used to construct a morpholino backbone.

Exemplary subunit structures for antisense oligonucleotides of the invention include the morpholino subunit types shown in FIGS. 1A-D, each linked by an uncharged, phosphorous-containing subunit linkage, as shown in FIGS. 2A-2D, respectively. In these figures, the X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Alkyl, alkoxy and thioalkoxy preferably include 1-6 carbon atoms, and more preferably 1-4 carbon atoms. Monosubstituted or disubstituted nitrogen preferably refers to lower alkyl substitution, and the cyclic structures are preferably 5- to 7-membered nitrogen heterocycles optionally containing 1-2 additional heteroatoms selected from oxygen, nitrogen, and sulfur. Z is sulfur or oxygen, and is preferably oxygen.

Figure 1B:
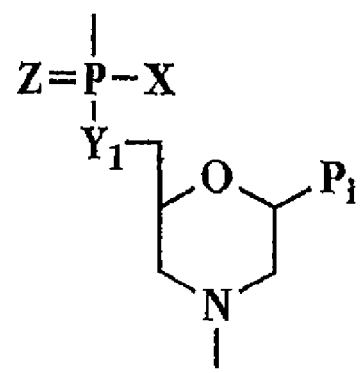
Figure 2A:
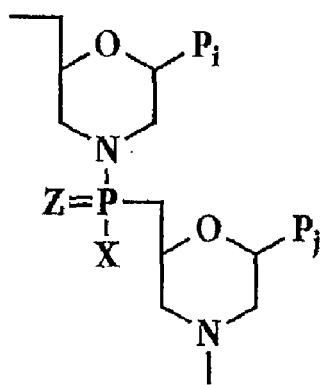
FIGS. 2A-D show the repeating subunit segment of exemplary morpholino oligonucleotides, designated A through D, constructed using subunits A-D, respectively, of FIG. 1.
Figure 2B:
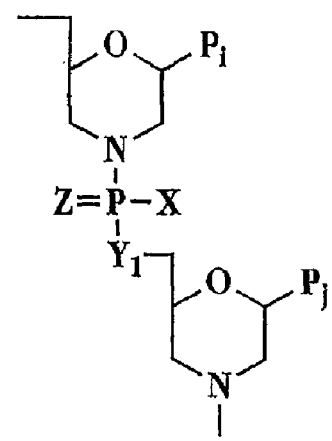

FIG. 1A shows a phosphorous-containing linkage which forms the five atom repeating-unit backbone shown in FIG. 2A, where the morpholino rings are linked by a 1-atom phosphoamide linkage. Subunit B in FIG. 1B is designed for 6-atom repeating-unit backbones, as shown in FIG. 2B. In FIG. 1B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Z is sulfur or oxygen, and is preferably oxygen. Particularly preferred morpholino oligonucleotides include those composed of morpholino subunit structures of the form shown in FIG. 2B, where X is an amine or alkyl amine of the form $X=NR_2$, where R is independently H or $CH_3$, that is where $X=NH_2$, $X=NHCH_3$ or $X=N(CH_3)_2$, $Y=O$, and $Z=O$.

Figure 1C:
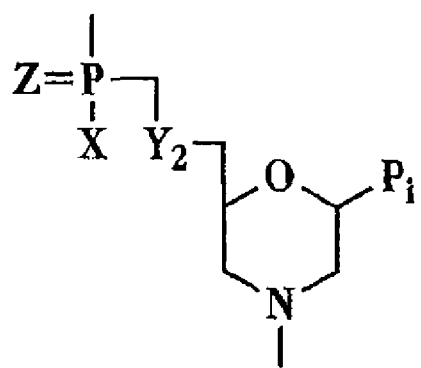
Figure 1D:
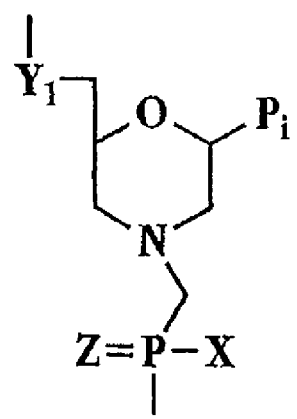
Figure 2C:
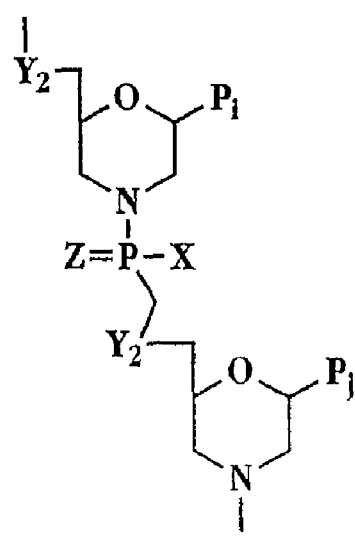
Figure 2D:
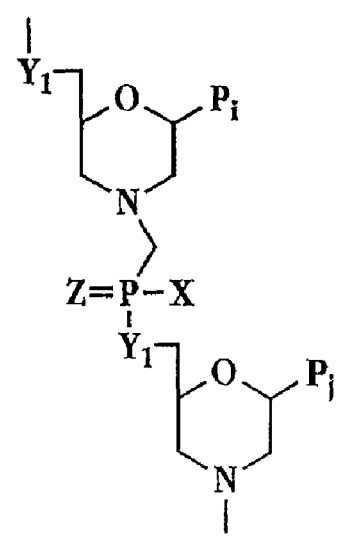
Figure 3A:
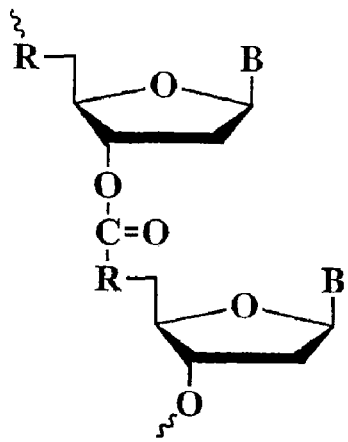
FIGS. 3A-3G show examples of uncharged linkage types in oligonucleotide analogs.
Figure 3B:
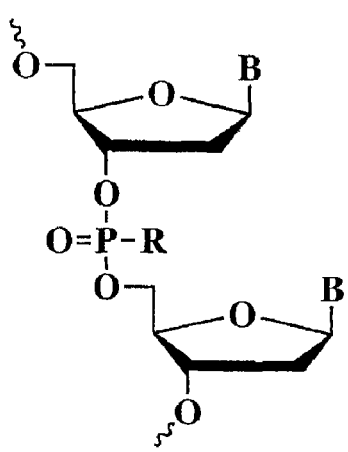
Figure 3C:
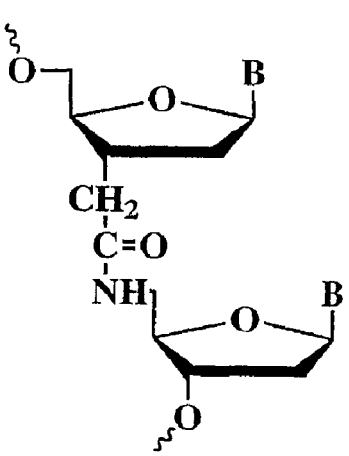
Figure 3D:
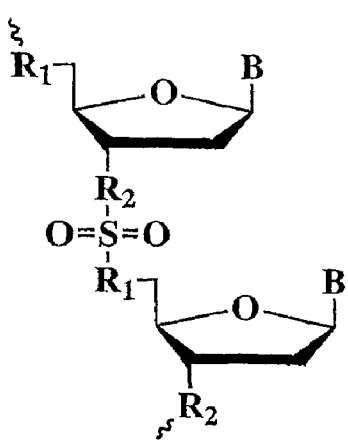
Figure 3E:
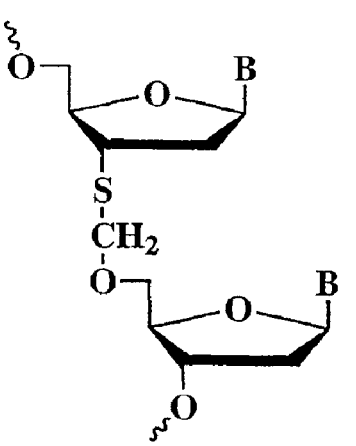
Figure 3F:
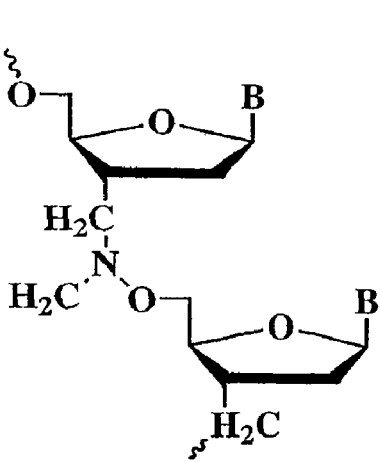
Figure 3G:
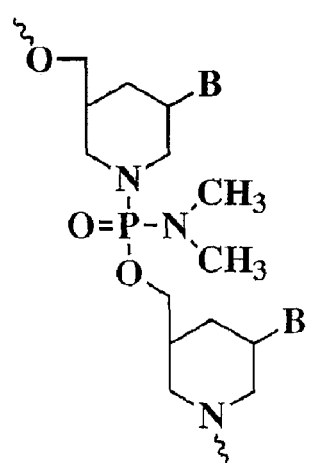

Subunits C-D in FIGS. 1C-D are designed for 7-atom unit-length backbones as shown for structures in FIGS. 2C and D. In Structure C, the X moiety is as in Structure B, and the moiety Y may be methylene, sulfur, or preferably oxygen. In Structure D, the X and Y moieties are as in Structure B. In all subunits depicted in FIGS. 1 and 2, each Pi and Pj is a purine or pyrimidine base-pairing moiety effective to bind, by base-specific hydrogen bonding, to a base in a polynucleotide, and is preferably selected from adenine, cytosine, guanine and uracil.

As noted above, the substantially uncharged oligomer may advantageously include a limited number of charged linkages, e.g. up to about 1 per every 5 uncharged linkages. In the case of the morpholino oligomers, such a charged linkage may be a linkage as represented by any of FIGS. 2A-D, preferably FIG. 2B, where X is oxide (—O—) or sulfide (—S—).

More generally, the morpholino oligomers with uncharged backbones are shown in FIGS. 3A-3G. Especially preferred is a substantially uncharged morpholino oligomer such as illustrated by the phosphorodiamidate morpholino oligomer (PMO) shown in FIG. 3G. It will be appreciated that a substantially uncharged backbone may include one or more, e.g., up to 10-20% of charged intersubunit linkages, typically negatively charged phosphorous linkages.

Antisense sequence. In the methods of the invention, the antisense oligomer is designed to hybridize to a region of the target nucleic acid sequence, under physiological conditions with a Tm substantially greater than 37° C., e.g., at least 50° C. and preferably 60° C.-80° C., wherein the target nucleic acid sequence is preferentially expressed in activated lymphocytes. The oligomer is designed to have high-binding affinity to the target nucleic acid sequence and may be 100% complementary thereto, or may include mismatches, e.g., to accommodate allelic variants, as long as the heteroduplex formed between the oligomer and the target nucleic acid sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to a nucleic acid sequence that is preferentially expressed in activated lymphocytes, it is effective to stably and specifically bind to the target sequence such that expression of the target sequence is modulated. The appropriate length of the oligomer to allow stable, effective binding combined with good specificity is about 8-40 nucleotide base units, and preferably about 12-25 nucleotides. Oligomer bases that allow degenerate base pairing with target bases are also contemplated, assuming base-pair specificity with the target is maintained.

mRNA transcribed from the relevant region of a gene associated with cFLIP expression is generally targeted by the antisense oligonucleotides for use in practicing the invention, however, in some cases double-stranded DNA may be targeted using a non-ionic probe designed for sequence-specific binding to major-groove sites in duplex DNA. Such probe types are described in U.S. Pat. No. 5,166,315 (Summerton et al., 1992), which is hereby incorporated by reference, and are generally referred to herein as antisense oligomers, referring to their ability to block expression of target genes.

In one general embodiment designed to target the start site of the processed human cFLIP transcript, the antisense compound has a base sequence that is complementary to a target region containing at least 12 contiguous bases in a processed human cFLIP transcript, in the target region from about −30 to +30 bases with respect to the AUG start site at position 0, and which includes at least 6 contiguous bases of one of the sequences identified by SEQ ID NOS:4-6. Exemplary antisense sequences include those identified as SEQ ID NOS:17-19.

In another general embodiment designed to target a splice site of preprocessed human cFLIP, the antisense compound has a base sequence that is complementary to a target region containing at least 12 contiguous bases in a preprocessed human cFLIP transcript, and which includes at least 6 contiguous bases of one of the sequences identified by SEQ ID NOS:7-15. Exemplary antisense sequences include those identified as SEQ ID NOS:20-28.

However, in some cases, other regions of the CFLIP mRNA (SEQ ID NO: 16) may be targeted, including one or more of, an initiator or promoter site, a 3'-untranslated region, and a 5-untranslated region. Both spliced and unspliced, pre-processed RNA may serve as the template for design of antisense oligomers for use in the methods of the invention.

When the antisense compound is complementary to a specific region of a target gene (such as the region surrounding the AUG start codon of the cFLIP gene) the method can be used to monitor the binding of the oligomer to the cFLIP RNA.

The antisense compounds for use in practicing the invention can be synthesized by stepwise solid-phase synthesis, employing methods detailed in the references cited above. The sequence of subunit additions will be determined by the selected base sequence. In some cases, it may be desirable to add additional chemical moieties to the oligomer compounds, e.g. to enhance the pharmacokinetics of the compound or to facilitate capture or detection of the compound. Such a moiety may be covalently attached, typically to the 5'- or 3'-end of the oligomer, according to standard synthesis methods. For example, addition of a polyethyleneglycol moiety or other hydrophilic polymer, e.g., one having 10-100 polymer subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an oligomer antisense, it is generally of course desirable to select chemical compounds of groups that are biocompatible and likely to be tolerated by cells in vitro or in vivo without undesirable side effects.

B. rTAT Peptide

The use of arginine-rich peptide sequences conjugated to PMO has been shown to enhance cellular uptake in a variety of cells (Wender, Mitchell et al. 2000; Moulton, Hase et al.

2003; Moulton and Moulton 2003) (ALSO -Moulton 2003 provisional patent application).

In studies conducted in support of the present invention, several different "arginine-rich" peptide sequences were conjugated to fluorescent tagged PMO (PMO-fl) and examined to determine the effect of peptide sequence on uptake into lymphocytes. Enhanced uptake was observed for all arginine-rich peptide-PMO conjugates tested compared to unconjugated PMO. The P003 arginine-rich peptide [NH2-RRRRRRRRRFFC—COOH] (SEQ ID NO:2) provides enhanced uptake into lymphocytes regardless of the cell activation state. However, among the arginine-rich peptides examined, only the rTAT (P002) peptide [NH$_2$-RRRQR-RKKRC—COOH] (SEQ ID NO:1) PMO conjugates exhibited differential uptake into lymphocytes dependent on cell activation status. PMO uptake was greatly increased in mature dendritic cells as well as activated B cells and CD4 and CD8 T cells when compared to immature or naive lymphocytes, as discussed below.

The rTAT peptide can be synthesized by a variety of known methods, including solid-phase synthesis. The amino acid subunits used in construction of the polypeptide may be either l- or d-amino acids, preferably all l-amino acids or all d-amino acids. Minor (or neutral) amino acid substitutions are allowed, as long as these do not substantially degrade the ability of the polypeptide to enhance uptake of antisense compounds selectively into activated T cells. One skilled in the art can readily determine the effect of amino acid substitutions by construction a series of substituted rTAT polypeptides, e.g., with a given amino acid substitution separately at each of the positions along the rTAT chain (see Example 1). Using the above test for uptake of fluoresceinated PMO-polypeptide conjugate, (see Example 2) one can then determine which substitutions are neutral and which significantly degrade the transporter activity of the peptide. Rules for neutral amino acid substitutions, based on common charge and hydrophobicity similarities among distinct classes of amino acids are well known and applicable here. In addition, it will be recognized that the N-terminal cysteine of SEQ ID NO: 1 is added for purposes of coupling to the antisense compound, and may be replaced/deleted when another terminal amino acid or linker is used for coupling.

The rTAT polypeptide can be linked to the compound to be delivered by a variety of methods available to one of skill in the art. The linkage point can be at various locations along the transporter. In selected embodiments, it is at a terminus of the transporter, e.g., the C-terminal or N-terminal amino acid. In one exemplary approach, the polypeptide has, as its N terminal residue, a single cysteine residue whose side chain thiol is used for linking. Multiple transporters can be attached to a single compound if desired.

When the compound is a PMO, the transporter can be attached at the 5' end of the PMO, e.g. via the 5'-hydroxyl group, or via an amine capping moiety, as described in Example 1C. Alternatively, the transporter may be attached at the 3' end, e.g. via a morpholino ring nitrogen, as described in Example 1D, either at a terminus or an internal linkage. The linker may also comprise a direct bond between the carboxy terminus of a transporter peptide and an amine or hydroxy group of the PMO, formed by condensation promoted by e.g. carbodiimide.

Linkers can be selected from those which are non-cleavable under normal conditions of use, e.g., containing a thioether or carbamate bond. In some embodiments, it may be desirable to include a linkage between the transporter moiety and compound which is cleavable in vivo. Bonds which are cleavable in vivo are known in the art and include, for example, carboxylic acid esters, which are hydrolyzed enzymatically, and disulfides, which are cleaved in the presence of glutathione. It may also be feasible to cleave a photolytically cleavable linkage, such as an oitho-nitrophenyl ether, in vivo by application of radiation of the appropriate wavelength.

For example, the preparation of a conjugate having a disulfide linker, using the reagent N-succinimidyl 3-(2-pyridyidithio) propionate (SPDP) or succinimidyloxycarbonyl α-methyl-α-(2-pyridyidithio) toluene (SMPT), is described in Example 1E. Exemplary heterobifunctional linking agents which further contain a cleavable disulfide group include N-hydroxysuccinimidyl 3-[(4-azidophenyl)dithio] propionate and others described in (Vanin).

IV. Selective Uptake of rTAT-Antisense into Activated T Cells

The present invention provides a method and composition for delivering therapeutic compounds, e.g., uncharged antisense compounds, specifically to activated immune cells, e.g., antigen-activated T cells, B cells, and mature dendritic cells.

Figures 4A, 4B, 4C:
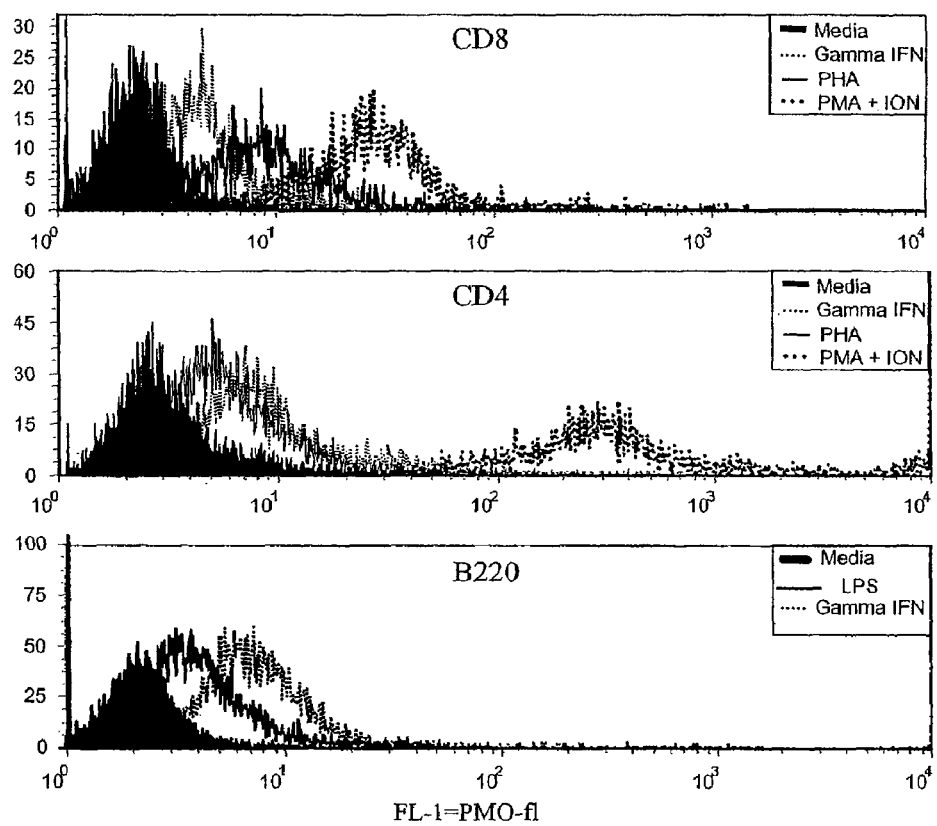
FIGS. 4A-4C show fluorescence activated cell sorting (FACS) analysis of uptake of rTAT-PMO conjugates into cultured splenocytes incubated with fluorescent conjugate and subjected to various lymphocyte activating substance in culture, as indicated. Separate lymphocytes populations were stained with antibodies to determine the extent of uptake by FACS analysis in CD8 positive T cells (FIG. 4A), CD4 positive T cells (FIG. 4B), and B cells (B220 positive cells) (FIG. 4C).

The ability of the rTAT peptide to enhance uptake of a fluoresceinated PMO antisense compound selectively into activated mouse lymphocytes is demonstrated in the study described in Example 2, and with the results shown in FIGS. 4A-4C. In this study, cultured mouse splenocytes were incubated with fluorescent rTAT-PMO conjugate and subjected to various lymphocyte activating substances, as indicated in the drawings. Separate lymphocyte populations (CD8 positive T cells, CD4 positive T cells, and B cells (B220 positive cells) were stained with antibody to determine the extent of uptake by FACS analysis of the cells. The results show relatively low uptake of the antisense PMO into non-activated cells (dark heavy line) in all three cell types. Activation by gamma-interferon (gamma-IFN), phytohemaglutinin (PHA) or phorbol myristic acid+calcium ionophore (PMA+ION) caused significantly increased uptake of the antisense into CD8 and CD 4 T cells. Likewise, activation of B cells with lipopolysaccharide (LPS) or gamma-IFN resulted in a significant enhancement of the rTAT-PMO into B cells.

The property of activation-dependent uptake of peptide-antisense conjugate is not observed with other arginine-rich peptides, which are known to enhance drug transport into cells. This is demonstrated by a second study described in Example 2, and with the results shown in FIGS. 5A and 5B. As seen in these figures, P003-PMO conjugate (corresponding to the arginine-rich peptide of SEQ ID NO: 2) is readily taken up by naive CD4 and naive CD8 T cells, PMO alone is relatively poorly taken up naive cells, and rTAT-PMO shows enhanced uptake into PHA treated cells.

In one aspect of the invention, therefore, the rTAT peptide may be conjugated to a substantially uncharged antisense compound, to enhance its uptake selectively into antigen-activated T cells, B cells, or dendritic cells, including antigen-activated human T, B, or dendritic cells.

V. Treating Transplantation Rejection and Autoimmune Disorder

The present invention provides the rTAT peptide (SEQ ID NO:1) that can target conjugated antisense oligomers to activated lymphocytes. By manipulating the immune system's normal mechanism for the generation of immune tolerance to self antigens, the present invention provides a method and composition that induces the obliteration of activated lymphocytes in the treatment of transplantation rejection or autoimmune disorders, such as multiple sclerosis, lupis, myathenia gravis, inflammatory bowel disease and rheumatoid arthritis.

The cFLIP gene is important in preventing AICD in lymphocytes that are activated by a legitimate foreign antigen and not a self-antigen. By combining the cell target specificity conferred by rTAT with an antisense oligomer to cFLIP (e.g., SEQ ID NOS:17-30), the present invention provides a means to precisely and specifically eliminate from the repertoire of the immune system those lymphocytes that are activated either by a transplanted tissue, chronically activated as in an autoimmune condition, or by an immunogenic therapeutic protein.

The utility of this combination of cell target specificity and an antisense blockade of cFLIP gene expression is important, in that provides a highly controllable therapy for inducing immune tolerance to foreign antigens. The therapy can be controlled with respect to time since the clearance of activated lymphocytes is only achieved while the cFLIP antisense compound is administered. It is also highly specific for only those lymphocytes that are recruited for activation by an immunogenic response since the P002 peptide conjugate delivers the antisense cFLIP oligomer to activated lymphocytes and not to other lymphocytes.

The normal immune response to a foreign antigen involves the clonal expansion of activated T and B cells that have specificity for the foreign antigen. Since the present invention provides a means to selectively purge these cells from the immune system, the immune tolerance so conferred would be long lived because the immune system is unable to replenish antigen-specific T cell clones once the antigen responsive precursor population is removed from the T cell repertoire.

A. c-FLIP Antisense and Antigen-Specific AICD

The ability of a c-FLIP antisense compound to promote antigen-specific AICD in activated cells is demonstrated by the study reported in Example 3, and with reference to FIGS. 6A-6C. In this study, splenocytes from DO.11 mice were treated with P003-cFLIP PMO (P003 arginine-rich transported peptide was employed since this peptide is known to promote antisense uptake into both activated and non-activated cells) or media control prior to co-culture with dendritic cells (DCs) presenting ovalbumin antigen or control DCs. In FIG. 6A, the level of expression of protease caspase-8 (FLICE) is indicated by the appearance of fluorescence signal from a fluoresceinated caspase-3 substrate. As seen in FIG. 6A, activation of the cells with DCs treated with ovalbumin and suppression of c-FLIP with antisense led to a marked increase in FLICE activity.

FIGS. 6B and 6C demonstrate the ability of c-FLIP antisense to promote apoptosis by inhibiting expression of c-FLIP in activated T cells. Cells treated with c-FLIP and activated with ovalbumin-treated DCs showed a significant increase propidium iodide staining (as an indicator or apoptosis) than non-activated either non-activated cells (FIG. 6B) or untreated, activated cells (FIG. 6C).

B. Treatment Methods

Figure 7A:
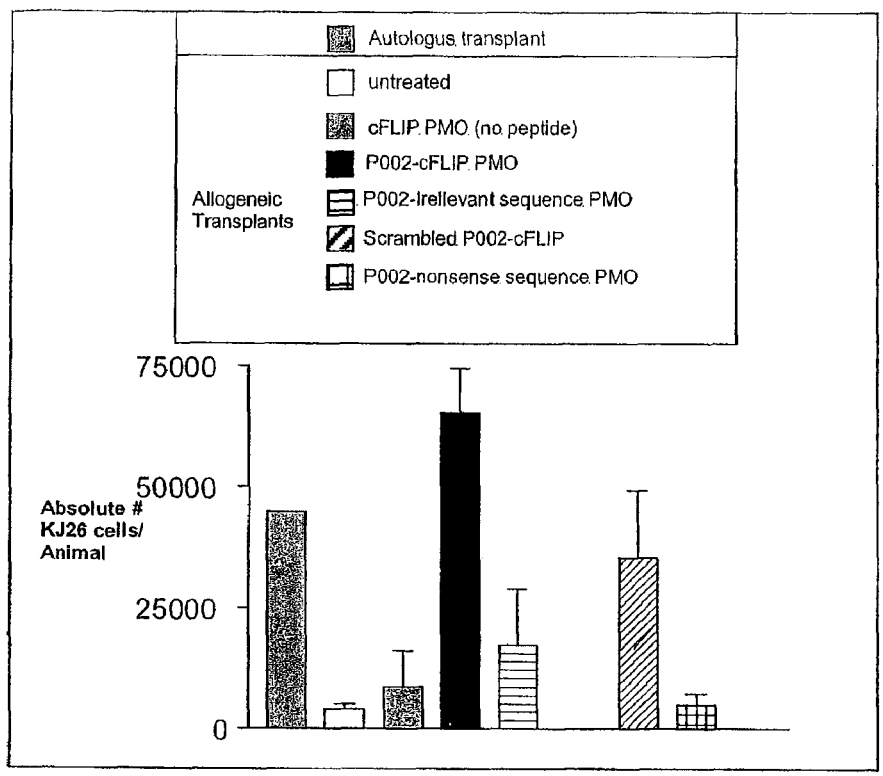
FIG. 7A is a bar graph showing the number of transplanted cells/animal from host animals treated with various PMO conjugates, and FIG. 7B demonstrates the survival of transplanted cells that retain functional activity.

An in vivo murine model for transplant acceptance was chosen to demonstrate the efficacy of the P002-cFLIP PMO to induce AICD in response to an alloantigen. The method is detailed in Example 4, and with reference to FIGS. 7A and 7B. Briefly, a transplant acceptance/survival model used cells expressing a minor histoincompatibility antigen (male antigen) to determine if CFLIP antisense treatment would promote transplant survival. Using male DO11.10 splenocytes as donor cells and female balb/c mice as recipients, groups of recipient mice were treated for 11 days with either cFLIP PMO, control PMOs or left untreated. 14 days post transplantation the recipients were sacrificed and the number of transplanted T cells in the spleen of each animal was determined by flow cytometry. The transplanted cells were detected using an antibody to the transgenic T cell receptor (KJ26) present in the DO11.10 mice. Functional activity of the surviving KJ26 positive cells was analyzed by intracellular cytokine staining in response to in vitro stimulation with ovalbumin. As seen in FIG. 7A, animals treated with the rTAT-c-FLIP PMO conjugate (P002-cFLIP PMO) gave significantly higher levels of functional KJ26 cells than any other treatment.

In one aspect, the invention is directed to methods of inducing immunological tolerance in vivo in a patient, by administering to the patient a therapeutically effective amount of a peptide-conjugated cFLIP PMO pharmaceutical composition, as described herein, e.g., a pharmaceutical composition comprising an antisense oligomer to cFLIP.

The antisense oligomers of the invention can be effective in the treatment of patients by modulating the immunological response to allogeneic transplantation or elimination of chronically activated T cells in the case of autoimmune diseases.

In one embodiment, a subject is in need of elimination of activated T cells responding to an allogeneic transplantation. In this embodiment, a cFLIP PMO is administered to the subject in a manner effective to result in purging the immune system of activated T cells. Typically, the patient is given treated with the conjugate shortly before, e.g., a few days before, receiving the transplant, then treated periodically, e.g., once every 14 days, until immunological tolerance is established. Immunological tolerance can be monitored during treatment by testing patient T cells for reactivity with donor MHC antigens in a standard in vitro test, as detailed below.

For the treatment of an autoimmune disorder, such as multiple sclerosis, lupis, myathenia gravis, inflammatory bowel disease and rheumatoid arthritis, the patient is given an initial single dose of the cFLIP antisense conjugate, then additional doses on a periodic basis, e.g., every 14 days, until improvement in the disorder is observed. As above, development of immunological tolerance can be monitored during treatment testing T cells from a blood sample for their ability to react with a selected, relevant antigen in vitro.

It will be understood that in vivo administration of such a cFLIP PMO is dependent upon, (1) the duration, dose and frequency of antisense administration, and (2) the general condition of the subject. A suitable dose can be approximated from animal model studies, such as the one reported in Example 4, and extrapolated to patient weight.

Typically, one or more doses of cFLIP antisense oligomer are administered, generally at regular intervals for a period of about one to two weeks. Preferred doses for oral administration are from about 1 mg oligomer/patient to about 25 mg oligomer/patient (based on an adult weight of 70 kg). In some cases, doses of greater than 25 mg oligomer/patient may be necessary. For IV administration, the preferred doses are from about 0.5 mg oligomer/patient to about 10 mg oligomer/patient (based on an adult weight of 70 kg).

The antisense agent is generally administered in an amount sufficient to result in a peak blood concentration of at least 200-400 nM antisense oligomer.

In general, the method comprises administering to a subject, in a suitable pharmaceutical carrier, an amount of a cFLIP morpholino antisense oligomer effective to inhibit expression of cFLIP or a factor that contributes to cFLIP expression.

Effective delivery of an antisense oligomer to the target nucleic acid is an important aspect of the methods described herein. In accordance with the invention, such routes of antisense oligomer delivery include, but are not limited to, inhalation; transdermal delivery; various systemic routes, including oral and parenteral routes, e.g., intravenous, subcutaneous, intraperitoneal, or intramuscular delivery.

It is appreciated that any methods which are effective to deliver a cFLIP PMO to the cells of an allogeneic transplant or to introduce the agent into the bloodstream are also contemplated.

In preferred applications of the method, the subject is a human subject and the methods of the invention are applicable to treatment of any condition wherein promoting immunological tolerance would be effective to result in an improved therapeutic outcome for the subject under treatment.

It will be understood that an effective in vivo treatment regimen using a cFLIP PMO in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

The method and composition of the present invention will also find use in combination with therapies that present a risk of immune response in a patient. For example, certain protein or peptide therapies may provoke an immune response that would otherwise limit the usefulness of the therapy over time. As another example, various gene therapy delivery vehicles may include viral vectors, such as adenovirus for targeting cancer cells, that may provoke an immune response that would otherwise limit the usefulness of the therapy. In these therapies, the rTAT-cFLIP conjugate is administered in conjunction with the immunogenic therapeutic agent, e.g., prior to and periodically during the course of the therapy. Alternatively, the conjugate may be administered only if an immune response begins to develop.

C. Administration of Anti-cFLIP Antisense Oligomers

Transdermal delivery of an antisense oligomer may be accomplished by use of a pharmaceutically acceptable carrier. One example of morpholino oligomer delivery is described in PCT patent application WO 97/40854, incorporated herein by reference.

In one preferred embodiment, the oligomer is an anti-cFLIP morpholino oligomer, contained in a pharmaceutically acceptable carrier, and delivered orally. In a further aspect of this embodiment, the antisense oligomer is administered at regular intervals for a short time period, e.g., daily for two weeks or less. However, in some cases the antisense oligomer is administered intermittently over a longer period of time.

It follows that a morpholino antisense oligonucleotide composition may be administered in any convenient vehicle, which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of an antisense oligonucleotide into cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, an oligonucleotide may be administered in microspheres or microparticles. (See, e.g., Wu et al., 1987).

Sustained release compositions are also contemplated within the scope of this application. These may include semi-permeable polymeric matrices in the form of shaped articles such as films or microcapsules.

D. Monitoring Treatment

The efficacy of a given therapeutic regimen involving the methods described herein, may be monitored, e.g., by conventional FACS assays for the phenotype of cells in the circulation of the subject under treatment. Such analysis is useful to monitor changes in the numbers of cells of various lineages, in particular, activated T and B cells in response to an allogeneic transplant.

Phenotypic analysis is generally carried out using monoclonal antibodies specific to the cell type being analyzed. The use of monoclonal antibodies in such phenotypic analyses is routinely employed by those of skill in the art for cellular analyses and monoclonal antibodies specific to particular cell types are commercially available.

The cFLIP PMO treatment regimen may be adjusted (dose, frequency, route, etc.), as indicated, based on the results of the phenotypic and biological assays described above.

From the foregoing, it will be appreciated how various objects and features of the invention are met. The specific elimination of self-reactive T cells or T cells capable of rejecting transplanted tissues is an important therapy for numerous human diseases where immunological tolerance is beneficial. The present invention provides a method of specifically purging the immune system of these cells through the use of antisense oligomers designed to inhibit cFLIP expression during the stage of antigen-specific activation. Antisense cFLIP mediated elimination of either chronically activated T cells (i.e. autoimmunity) or naive T cell responding to alloantigens (transplantation) provides a potent and specific therapeutic effect.

Additionally, this treatment method is long lived because the immune system is unable to replenish antigen-specific T cell clones once the precursor population is removed from the T cell repertoire. In addition, by specifically targeting the antisense cFLIP oligomer to activated T and B cells, resting immune cells would be unaffected, allowing for the patient to respond normally to foreign antigens as soon as the therapy is withdrawn. Moreover, the immune status of the patient prior to the cFLIP therapy (e.g. immunity provided by previous vaccinations or infections) would remain intact.

The following examples illustrate but are not intended in any way to limit the invention.

EXAMPLE 1

Preparation of rTAT-Antisense Conjugates

A. Production of PMO and peptide conjugated PMOs:

The PMOs were synthesized at AVI BioPharma (Corvallis, Oreg.) as previously described (Summerton and Weller, 1997). Purity of full length oligomers was >95% as determined by reverse-phase high-pressure liquid chromatography (HPLC) and MALDI TOF mass spectroscopy. Peptide conjugated forms of the PMO where produced by attaching the carboxy terminal cysteine of the peptide to the 5' end of the PMO through a cross-linker N-[γ-maleimidobutyryloxy] succinimide ester (GMBS) (Moulton and Moulton, 2003), as detailed below in section C. The peptides used in this study designated as P002 (RRRQRRKKRC, SEQ ID NO:1) (Moulton and Moulton, 2003) and P003 (RRRRRRRRRFFC, SEQ ID NO:2). The lyophilized PMO or peptide-conjugated PMO were dissolved in sterile $H_2O$ prior to use in cell cultures or dilution in PBS prior to injection in to mice.

B. 3'- Fluoresceination of a PMO (Phosphorodiamidate-Linked Morpholino Oligomer).

A protected and activated carboxyfluorescein, e.g. 6-carboxyfluorescein dipivalate N-hydroxysuccinimide ester, commercially available from Berry & Associates, Inc. (Dexter, Mich.), was dissolved in NMP (0.05M), and the solution was added to a PMO synthesis column in sufficient volume to cover the resin. The mixture was incubated at 45° C. for 20 minutes, then the column was drained and a second similar portion of protected and activated carboxyfluorescein was added to the column and incubated at 45° C. for 60 minutes. The column was drained and washed with NMP, and the oligomer was cleaved from the resin using 1 ml of cleavage solution (0.1 M dithiothreitol in NMP containing 10% triethylamine). The resin was washed with 300 µl of cleavage solution three times, immediately followed by addition of 4 ml of concentrated ammonia hydroxide and 16 hours incubation at 45° C. to remove base protecting groups. The morpholino oligomer was precipitated by adding 8 volumes of acetone, the mixture was centrifuged, and the pellet was washed with 15 ml of $CH_3CN$. The washed pellet was redissolved in 4 ml of $H_2O$ and lyophilized. The product was analyzed by time-of-flight MALDI mass spectrometry (MALDI-TOF) and high pressure liquid chromatography (HPLC). C. 2.3'-Acetylation of PMO and 5' Attachment of Transport Peptide.

Acetic anhydride (0.1 M), dissolved in N-methyl-2-pyrrolidinone (NMP) containing 1% N-ethyl morpholine (v/v) was added while the oligomer was still attached to the synthesis resin. After 90 minutes at room temperature, the oligomer was washed with NMP, cleaved from the synthesis resin and worked up as described above. The product was analyzed by time-of-flight MALDI mass spectrometry (MALDI-TOF) and high pressure liquid chromatography (HPLC). The desired product included a 3'-acetyl group and was capped at the 5'-end with piperazine, which was used for conjugation, as described below.

The cross linker, N-(γ-maleimidobutyryloxy)succinimide ester (GMBS), was dissolved in 50 µl of DMSO, and the solution was added to the oligomer (2-5 mM) in sodium phosphate buffer (50 mM, pH 7.2) at a 1:2 PMO/GMBS molar ratio. The mixture was stirred at room temperature in the dark for 30 minutes, and the product was precipitated using a 30-fold excess of acetone, then redissolved in water. The PMO-GMBS adduct was lyophilized and analyzed by MALDI-TOF and HPLC. The adduct was then dissolved in phosphate buffer (50 mM, pH 6.5, 5 mM EDTA) containing 20% $CH_3CN$, and the transport peptide was added, at a 2:1 peptide to PMO molar ratio (based on a PMO concentration as determined by its absorbance at 260 nm). The reaction was stirred at room temperature in the dark for 2 hours. The conjugate was purified first through a CM-Sepharose (Sigma, St. Louis, Mo.) cationic exchange column, to remove unconjugated PMO, then through a reverse phase column (HLB column, Waters, Milford, Mass.). The conjugate was lyophilized and analyzed by MALDI-TOF and capillary electrophoresis (CE). The final product contained about 70% material corresponding to the full length PMO conjugated to the transport peptide, with the balance composed of shorter sequence conjugates, a small amount of unconjugated PMO, both full length and fragments, and a very small amount (about 2%) of unconjugated peptide. The concentration determination used for all experiments was based on the total absorbance at 260 nm, including all shorter PMO sequences in the sample.
D. 3'-Attachment of Transport Peptide.

A PMO having a free secondary amine (ring nitrogen of morpholine) at the 5'-end was dissolved in 100 mM sodium phosphate buffer, pH 7.2, to make a 2-5 mM solution. The linking reagent, GMBS, was dissolved in 100 µ of DMSO and added to the PMO solution at a PMO/GMBS ratio of 1:2. The mixture was stirred at room temperature in the dark for 30 min, then passed through a P2 (Biorad) gel filtration column to remove the excess GMBS and reaction by-products.

The GMBS-PMO adduct was lyophilized and re-dissolved in 50 mM phosphate buffer, pH 6.5, to make a 2-5 mM solution. A transport peptide having a terminal cysteine was added to the GMBS-PMO solution at a molar ratio of 2:1 peptide to PMO. The reaction mixture was stirred at room temperature for 2 hours or at 4° C. overnight. The conjugate was purified by passing through Excellulose gel filtration column (Pierce Chemical) to remove excess peptide, then through a cation exchange CM-Sepharose column (Sigma) to remove unconjugated PMO, and finally through an Amberchrom reverse phase column (Rohm and Haas) to remove salt. The conjugate was lyophilized and characterized by MS and HPLC.
E. Preparation of a PMO-Peptide Conjugate Having a Cleavable Linker The procedure of sections C or D is repeated, employing N-succinimidyl 3-(2-pyridyldithio) propionate (SPDP) or succinimidyloxycarbonyl α-methyl-α-(2-pyridyldithio) toluene (SMPT) as linking reagent place of GMBS.

EXAMPLE 2

Uptake Of rTAT-Antisense Conjugates Selectively Into Activated T Cells

The DO11.10 transgenic mouse system (Murphy, Heimberger et al. 1990) was used as a source of splenocytes and T cells. This transgenic mouse contains the gene for the T cell receptor (TCR) from the T cell hybridoma, DO11.10, that recognizes chicken ovalbumin (OVA). Virtually all thymocytes and peripheral T cells in these mice express the OVA-TCR which is detected by the KJ26 monoclonal antibody.
A. Uptake in Naïve and Activated Murine Lymphocytes Freshly isolated splenocytes from B6 mice were plated (1.5 million/well) into 96 well V-bottom plates and incubated with PMO-fl, P002-PMO-fl or P003-PMO-fl [10 µM, 10 µM and 5 µM in culture media, respectively]. Lymphocyte activating substances derived from bacterial (LPS), murine cytokine (Gamma IFN), mitogenic plant lectin (PHA), chemical activator (PMA+ION) or culture media control (naive cell treatment) were added to individual cultures as follows; LPS [1 µg/ml] (lipopolysaccharide), murine gamma interferon [10 ng/ml], PHA (phytohemaglutanin) [2.5 µg/ml], PMA (phorbol myristic acid)+calcium ionophore [10 ng/ml+5 ng/ml] or RPMI+10% fetal calf serum. All activating substances were added to cells with the PMO treatment overnight save the PMA+calcium ionophore which was added 4 hours prior to staining the cells for flow cytometric analysis. Immediately following treatment the cultures were washed twice with cold FACS buffer (phosphate buffered saline+1% fetal calf serum+0.02% w/v sodium azide). All cultures were suspended in 100 µls of Fc blocking antibody (eBioscience) [0.5 µg/well] for 15 min on ice. Staining of lymphocyte populations was performed using anti-CD4 or anti CD8 PE-Texas Red [0.3 µg/million cells] (CalTag) or anti-CD45R (clone B220) APC (eBioscience) [0.4 mg/million cells] for 30 min on ice. The cells were washed twice with cold FACS buffer and suspended in 50 µl of cold cyofix/cytoperm reagent (Pharmingen) for 30 min to lyse remaining red blood cells. The cells were washed once with FACS buffer and suspended in 200 µl FACS buffer prior to analysis. Cell staining and PMO-fl uptake was measured using a FACSCalibur flow cytometer (Becton Dickinson). Flow data was analyzed using FCS Express 2 Pro software (Denovo software).

FIGS. 4A-4C demonstrate that separate lymphocytes populations all have enhanced uptake of P002-PMO conjugate when activated by a variety of lymphocyte activators. Different lymphocyte populations were stained with antibodies to determine the extent of uptake by FACS analysis in T cells A) CD8 positive T cells, B) CD4 positive T cells and C) B cells (B220 positive cells).

Figure 5A:
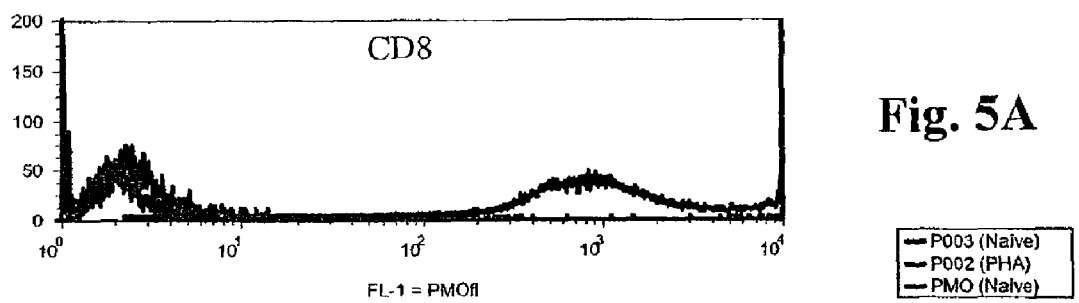
FIGS. 5A-5B shows FACS analysis of conjugate uptake into CD8 (FIG. 5A), and CD4 (FIG. 5B) of PMO-0003 (arginine-rich peptide-PMO) and PMO-0002 (rTAT-PMO) in naive and activated T cells.
Figure 5B:
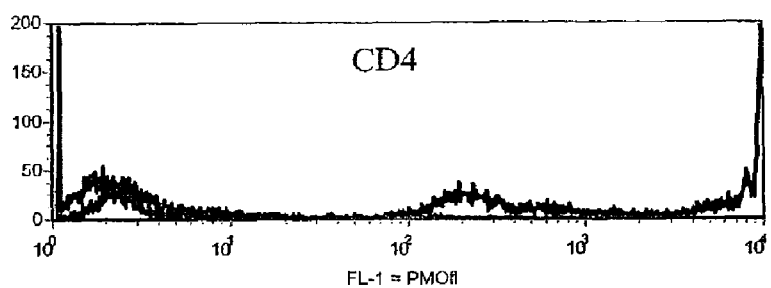

FIGS. 5A and 5B are similar to FIGS. 4A-4C except that P003-PMO-fl was compared to P002-PMO-fl and unconjugated PMO-fl in A) CD8 positive T cells and B) CD4 positive T cells. The P002-PMO-fl treated cells were activated with PHA as described above. The figure indicates that the P003 peptide greatly enhances uptake in naive T-cells of both CD4 and CD8 lineages compared to PHA-activated T-cells treated with P002-PMO-fl. Uptake of the PMO-fl without a peptide conjugate is undetectable.

EXAMPLE 3

Antigen-Specific AICD In Ovalbumin-Specific T Cells After Treatment With cFLIP-PMO This example demonstrates an in vitro analysis of cFLIP-PMO activity in activated T cells. Dendritic cells (DCs) used to present ovalbumin (OVA) to T cells were derived from bone marrow cells extracted from the tibia and femurs of balb/c mice and cultured for 8 days in RPMI +10% FBS containing recombinant murine GM-CSF (Granulocyte/monocyte colony stimulating fact-or) [25 ng/ml] and lnterleukin-4 [ 5 ng/ml]. DCs used to present ovalbumin were pulsed with OVA fraction VII (Sigma) [200 ug/ml] in culture media overnight or control (no antigen). DCs were matured by adding LPS [1 µg/ml] during the overnight incubation. Freshly isolated splenocytes from DO11.10 mice were treated with P003-cFLIP (SEQ ID NO:30) [25 µM] or media control overnight. The next day the splenocyte cultures were washed twice with RPMI and then co-cultured with either OVA-pulsed DCs or control DCs for 4 hours. To examine loss of membrane integrity of the OVA-specific T cells after treatment with P003-cFLIP some of the DC-splenocyte co-cultures were incubated with propidium iodide [50 ng/ml] for the last 5 min of culturing. The cultures were then Fc blocked, stained with anti-TCR KJ26 TriC (CalTag) [1.0 ug/million cells] and analyzed by FACS. To measure caspase-3 activity the co-cultures were incubated with CytoxiLux substrate (Oncolmmunin, Inc.) during the final hour of the co-culture incubation. The CytoxiLux substrate is cleaved by caspase-3 to yield a fluorescent product. These samples were processed as above and analyzed by FACS.

FIG. 6A is a FACS analysis of caspase-3 induction in cFLIP-PMO-treated T cells after co-culture with DCs presenting OVA compared to media control DCs. FIGS. 6B and 6C similarly demonstrate activation of AICD by analyzing uptake of propidium iodide as a measure of early apoptotic processes.

EXAMPLE 4

Therapeutic Treatment Of Transplant Recipients With rTAT-cFLIP PMO

Figure 7B:
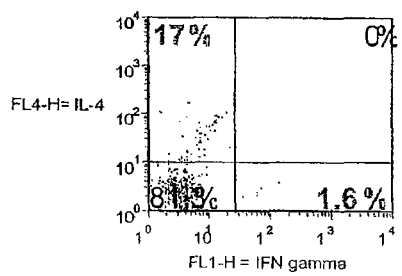

This study was performed to determine if antisense P002-cFLIP PMO (SEQ ID NO:29) can be applied therapeutically to eliminate or diminish allotypic responses during transplantation and thus promote transplant survival. Female balb/c mice were treated with P002-cFLIP PMO, control PMOs or left untreated 3 days prior to and 7 days after transplantation of male DO11.10 splenocytes. The animals were sacrificed 14 days post transplantation and spleens examined for the presence of KJ26 positive T cells by FACS analysis. FIG. 7A represents the average total number of surviving KJ26 positive cells for each treatment group. FIG. 7B shows the functional activity of the transplanted KJ26 T cells in the P002-cFLIP PMO treated mice as examined by intracellular cytokine staining after culturing the recipients splenocytes with ovalbumin.

A. Treatment Groups

| Treatment Group | # of recipient mice |
|---|---|
| Untreated control | 4 |
| P002-cFLIP PMO conjugate (SEQ ID NO: 29) | 4 |
| Irrelevant target sequence P002 PMO conjugate | 4 |
| Female transplant control (Autologous) | 2 |
| cFLIP PMO (no peptide) (SEQ ID NO: 29) | 4 |
| P002 nonsense scramble PMO | 3 |
| P002-cFLIP scramble PMO (SEQ ID NO: 31) | 4 |

Donor mice = male & female DO11.10 (avg. age 12 weeks)
Recipient mice = female BALB/c (6-8 week)

B. PMO Delivery: 300 µg of the appropriate PMO agent was delivered by intraperitoneal injection in 100 µl of PBS into each mouse on days -3, -1, and day 0,1,2,3, & 6 relative to the transplant. The PMO concentration was decreased to 200 µg on day 7, and continued days 8,9, & 10.

C. Transplantation Protocol:

Spleens were extracted from 18 male and 2 female DO11.10 mice on the day before the transplant and suspended separately in culture at 37° C. overnight in complete RPMI media (+10% FBS+1% Penstrep+50 pM Beta-Mercaptoethanol+200 µM L-glutamine.) On the day of the transplant, recipient BALB/c mice were anesthetized with isofluorane. Cells were transplanted by delivering 19×10$^6$ DO11.10 male splenocytes in 100 µls PBS into the retrorbital sinus cavity of each mouse with a 25 G ½" needle. Two recipient BALB/c mice received 19×10$^6$ female DO11.10 splenocytes by the same route. After 14 days, each recipient mouse was weighed, numbered, and anesthetized prior to performing a retrorbital bleed. The mice were then euthanized by $CO_2$ affixation, and spleens were collected from each recipient mouse. Serum was isolated through centrifugation and frozen at −80 C.

D. Determination of Transplant Success

Spleens were harvested and single cell suspension made by straining through a 100 µm sieve. Cells were washed with DMEM+1% FBS, and suspended in 5 ml of the same media. 100 µl of each splenocyte suspension was transferred to a 96-well plate, and incubated 10 min with RBC lysis buffer (eBioscience). Theses cells were counted and remaining suspended at 5×10$^6$/ml in complete RPMI media. Five million cells from each suspension were transferred to a single well of a 96-well plate. Cells were centrifuged at 1000 RPM for 5 min, washed 2×x in 200 µl of PBS+1% FBS, and suspended in FC block at 4° C. overnight. Each sample well was processed for FACS analysis to determine the number of KJ26 positive in the spleens of each animal. Briefly, the cells were washed, Fc Blocked (as described above) and stained with anti-CD4 TriC [1 µg/million cells] (CalTag) and anti-KJ26 FITC [2.5 µg/million cells] for 40 min. on ice. The red blood cells were lysed (as described above). Stained splenocytes from a male DO11.10 mouse served as a gating control in the FACS analysis. Approximately, one million events within the live lymphocyte gate were examined for each sample to enumerate the KJ26 positive cells present. The total surviving KJ26 positive cells was computed by multiplying the percentage of cells within the live gate to the total events collected by the total number or splenocytes enumerated for the particular recipient examined. FIG. 7A graphically represent these data.

E. Functionality of donor cells: Post transplantation splenocytes were prepared as described above. 500 µl of each splenocyte suspension was added to 2 wells each of a 24-well plate. Ovalbumin [200 µg/ml] in 100 µl was added to 1 well and 100 µl media to the other for 24 hr. The final 4 hr Golgi-Plug (Pharmingen) was added to each well. The cells were the processed for intracellular cytokine detection by FACS analysis. Cells were removed to 96 well V-bottom plates and Fc Blocked and stained with anti-KJ26 (as described above). Cytokine production was detected by permeabilization of the cell membranes with CytoFix/CytoPerm reagent (Pharmingen) and staining with anti-IL4 APC [0.5 µg/million cells] and anti-gamma interferon FITC [2 mg/million cells] (both from Pharmingen). Cells were gated of KJ26 positive region and the percentage of cytokine positive KJ26 positive cells determined using flow analysis software. FIG. 7B represents an example of one mouse from the P002-cFLIP PMO treatment group responding to ovalbumin by production of IL-4 and gamma interferon. Cytokine production in cultures not pulsed with ovalbumin produced was <0.01% of the KJ26 cells.

Sequence Listing

For SEQ ID NO:7-15, "/" designates the junction of the exon and intron.

Peptide Sequences

1. SEQ ID NO:1, $NH_2$- RRRQRRKKRC—$CO_2H$ (P002, rTAT)
2. SEQ ID NO:2, $NH_2$- RRRRRRRRRFFC—$CO_2H$ (P003, $R_9F_2$)
3. SEQ ID NO:3, $NH_2$- RKKRRQRRRC—$CO_2H$ (TAT)

Target sequences (5' to 3'):

4. SEQ ID NO:4, −12 to +12 spanning the AUG start site region of cFLIP TCTAAGAGTAGGATGTCTGCTGAAG (470 to 495 of GenBank NM003879)
5. SEQ ID NO:5, −30 to −10 upstream of the start site region of cFLIP CCTTGTGAGCTTCCCTAGTCT (452 to 472 of GenBank NM003879)
6. SEQ ID NO:6, +10 to +30 downstream of the start site region of cFLIP GAAGTCATCCATCAGGTTGAA (492 to 512 of GenBank NM003879)
7. SEQ ID NO:7, Exon 4 splice donor region of preprocessed cFLIP CCTTGTTTCGGACTATAG/G (GenBank AB038967)
8. SEQ ID NO:8, Exon 5 splice acceptor region GGTTTG-CAGAGTGCTGATG/ (GenBank AB038968)
9. SEQ ID NO:9, Exon 5 splice donor region GATAAG-CAAGGAGAAAG/GTGAT (GenBank AB038968)
10. SEQ ID NO:10, Exon 6 splice acceptor region CTCT-TAG/AGTTTCTTGGACC (GenBank AB038968)
11. SEQ ID NO:11, Exon 6 splice donor region CCAGAAG-TACAAGCAGTCTG/G (GenBank AB038968)
12. SEQ ID NO:12, Exon 7 splice acceptor region TCT-GCTTTTATAG/TTCAAGG (GenBank AB038969)
13. SEQ ID NO:13, Exon 7 splice donor region GGATCCT-TCAAATAACTTCAGG/ (GenBank AB038969)
14. SEQ ID NO:14, Exon 8 splice acceptor region CTTCTA-CAG/ATGATAACACC (GenBank AB038969)
15. SEQ ID NO:15, Exon 9 splice acceptor region GAAG/CTCCATAATGGG (GenBank AB038970)
16. SEQ ID NO:16, entire processed cFLIP transcript (GenBank NM003879)

```
   1 GGACGTCGAG GCATTACAAT CGCGAAACCA AGC-
     CATAGCA TGAAACAGCG AGCTTGCAGC
  61 CTCACCGACG AGTCTCAACT AAAAGGGACT
     CCCGGAGCTA GGGGTGGGGA CTCGGCCTCA
 121 CACAGTGAGT GCCGGCTATT GGACTTTTGT
     CCAGTGACAG CTGAGACAAC AAGGACCACG
 181 GGAGGAGGTG TAGGAGAGAA GCGCCGCGAA
     CAGCGATCGC CCAGCACCAA GTCCGCTTCC
 241 AGGCTTTCGG TTTCTTTGCC TCCATCTTGG
     GTGCGCCTTC CCGGCGTCTA GGGGAGCGAA
 301 GGCTGAGGTG GCAGCGGCAG GAGAGTCCGG
     CCGCGACAGG ACGAACTCCC CCACTGGAAA
 361 GGATTCTGAA AGAAATGAAG TCAGCCCTCA
     GAAATGAAGT TGACTGCCTG CTGGCTTTCC
 421 TGTTGACTGG CCCGGAGCTG TACTGCAAGA
     CCCTTGTGAG CTTCCCTAGT CTAAGAGTAG
 481 GATGTCTGCT GAAGTCATCC ATCAGGTTGA
     AGAAGCACTT GATACAGATG AGAAGGAGAT
 541 GCTGCTCTTT TTGTGCCGGG ATGTTGCTAT
     AGATGTGGTT CCACCTAATG TCAGGGACCT
 601 TCTGGATATT TTACGGGAAA GAGGTAAGCT
     GTCTGTCGGG GACTTGGCTG AACTGCTCTA
 661 CAGAGTGAGG CGATTTGACC TGCTCAAACG
     TATCTTGAAG ATGGACAGAA AAGCTGTGGA
 721 GACCCACCTG CTCAGGAACC CTCACCTTGT
     TTCGGACTAT AGAGTGCTGA TGGCAGAGAT
 781 TGGTGAGGAT TTGGATAAAT CTGATGTGTC
     CTCATTAATT TTCCTCATGA AGGATTACAT
 841 GGGCCGAGGC AAGATAAGCA AGGAGAAGAG
     TTTCTTGGAC CTTGTGGTTG AGTTGGAGAA
 901 ACTAAATTTG GTTGCCCCAG ATCAACTGGA
     TTTATTAGAA AAATGCCTAA AGAACATCCA
 961 CAGAATAGAC CTGAAGACAA AAATCCAGAA
     GTACAAGCAG TCTGTTCAAG GAGCAGGGAC
1021 AAGTTACAGG AATGTTCTCC AAGCAGCAAT
     CCAAAAGAGT CTCAAGGATC CTTCAAATAA
1081 CTTCAGGCTC CATAATGGGA GAAGTAAAGA
     ACAAAGACTT AAGGAACAGC TTG GCG CTCA
1141 ACAAGAACCA GTGAAGAAAT CCATTCAGGA
     ATCAGAAGCT TTTTTGCCTC AGAGCATACC
1201 TGAAGAGAGA TACAAGATGA AGAGCAAGCC
     CCTAGGAATC TGCCTGATAA TCGATTGCAT
1261 TGGCAATGAG ACAGAGCTTC TTCGAGACAC
     CTTCACTTCC CTGGGCTATG AAGTCCAGAA
1321 ATTCTTGCAT CTCAGTATGC ATGGTATATC CCA-
     GATTCTT GGCCAATTTG CCTGTATGCC
1381 CGAGCACCGA GACTACGACA GCTTTGTGTG
     TGTCCTGGTG AGCCGAGGAG GCTCCCAGAG
1441 TGTGTATGGT GTGGATCAGA CTCACTCAGG
     GCTCCCCCTG CATCACATCA GGAGGATGTT
1501 CATGGGAGAT TCATGCCCTT ATCTAGCAGG
     GAAGCCAAAG ATGTTTTTTA TTCAGAACTA
1561 TGIGGTGICA GAGGGCCAGC TGGAGAACAG
     CAGCCTCTTG GAGGTGGATG GGCCAGCGAT
1621 GAAGAATGTG GAATTCAAGG CTCAGAAGCG
     AGGGCTGTGC ACAGTTCACC GAGAAGCTGA
1681 CTTCTTCTGG AGCCTGTGTA CTGCGGACAT
     GTCCCTGCTG GAGCAGTCTC ACAGCTCACC
1741 GTCCCTGTAC CTGCAGTGCC TCTCCCAGAA
     ACTGAGACAA GAAAGAAAAC GCCCACTCCT
1801 GGATCTTCAC ATTGAACTCA ATGGCTACAT
     GTATGATTGG AACAGCAGAG TTTCTGCCAA
1861 GGAGAAATAT TATGTCTGGC TGCAGCACAC
     TCTGAGAAAG AAACTTATCC TCTCCTACAC
```

```
1921 ATAAGAAACC AAAAGGCTGG GCGTAGTGGC
     TCACACCTGT AATCCCAGCA CTTTGGGAGG
1981 CCAAGGAGGG CAGATCACTT CAGGTCAGGA
     GTTCGAGACC AGCCTGGCCA ACATGGTAAA
2041 CGCTGTCCCT AGTAAAAATG CAAAAATTAG
     CTGGGTGTGG GTGTGGGTAC CTGTGTTCCC
2101 AGTTACTTGG GAGGCTGAGG TGGGAGGATC
     TTTTGAACCC AGGAGTTCAG GGTCATAGCA
2161 TGCTGTGATT GTGCCTACGA ATAGCCACTG
     CATACCAACC TGGGCAATAT AGCAAGATCC
2221 CATCTCTTTA AAAAAAAAAA MA
```

Targeting sequences

17. SEQ ID NO:17, exemplary antisense sequence spanning the AUG start site 5'-CTTCAGCAGACATCCTACTC-3' (GenBank NM003879)
18. SEQ ID NO:18, exemplary antisense sequence to region 5' of the start site 5'-GACTAGGGAAGCTCACAAGG-3' (GenBank NM003879)
19. SEQ ID NO:19, exemplary antisense sequence to region 3' of the start site 5'-TCAACCTGATGGATGACTTG-3' (GenBank NM003879)
20. SEQ ID NO:20, exemplary antisense sequence to Exon 4 splice donor 5'-CCTATAGTCCGAAACAAGG-3' (GenBank AB038967)
21. SEQ ID NO:21, exemplary antisense sequence to Exon 5 splice acceptor 5'-CATCAGCACTCTGCAAACC-3' (GenBank AB038968)
22. SEQ ID NO:22, exemplary antisense sequence to Exon 5 splice donor 5'-CTCACCTTTCTCCTTGCTTATC-3' (GenBank AB038968)
23. SEQ ID NO:23, exemplary antisense sequence to Exon 6 splice acceptor 5'-GGTCCAAGAAACTCTAAGAG-3' (GenBank AB038968)
24. SEQ ID NO:24, exemplary antisense sequence to Exon 6 splice donor 5'-CCAGACTGCTTGTACTTCTGG-3' (GenBank AB038968)
25. SEQ ID NO:25, exemplary antisense sequence to Exon 7 splice acceptor 5'-CCTTGAACTATAAAAGCAGA-3' (GenBank AB038969)
26. SEQ ID NO:26, exemplary antisense sequence to Exon 7 splice donor 5'-CCTGAAGTTATTTGAAGGATCC-3' (GenBank AB038969)
27. SEQ ID NO:27, exemplary antisense sequence to Exon 8 splice acceptor 5'-GGTGTTATCATCTGTAGAAG-3' (GenBank AB038969)
28. SEQ ID NO:28, exemplary antisense sequence to Exon 9 splice acceptor 5'-CCCATTATGGAGCTTC-3' (GenBank AB038970)
29. SEQ ID NO:29, P002-antisense start-site sequence tested P002-CTGGGCCATGTTCAGAACC-3'
30. SEQ ID NO:30, P003-antisense start-site sequence tested P003-CTGGGCCATGTTCAGAACC-3'
31. SEQ ID NO:31, rTAT-scrambled antisense sequence tested P002-CGTGCGCTATGTGACACAC-3'

---

It is claimed:

1. An antisense conjugate for use in inducing immunologic tolerance in a subject, comprising
   (a) a substantially uncharged antisense oligonucleotide compound
      (i) composed of morpholino subunits and phosphorus-containing intersubunit linkages joining a morpholino nitrogen of one subunit to a 5' exocyclic carbon of an, adjacent subunit, and containing 20-25 subunits,
      (ii) comprising the base sequence identified by SEQ ID NO: 17,
      (iii) effective, when hybridized to the processed human cFLIP transcript, to block expression of cFLIP in lymphocytes, and
   (b) covalently coupled to the antisense oligonucleotide compound, an arginine-rich peptide effective to enhance the uptake of the antisense compound into lymphocytes.

2. The conjugate of claim 1, wherein the morpholino subunits are joined by phosphorodiamidate linkages, in accordance with the structure:

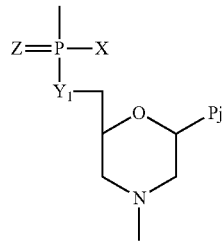

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino.

3. The conjugate of claim 2, wherein X=$NR_2$, where each R is independently hydrogen or methyl.

4. An antisense conjugate for use in inducing immunologic tolerance in a subject, comprising
   (a) a substantially uncharged antisense oligonucleotide compound
      (i) composed of morpholino subunits and phosphorus-containing intersubunit linkages joining a morpholino nitrogen of one subunit to a 5' exocyclic carbon of an adjacent subunit, and containing 12-40 subunits,
      (ii) having a base sequence that is complementary to at least 12 contiguous bases in a region extending from −30 to +30 bases with respect to the AUG start site in a processed human cFLIP transcript, corresponding to base positions 452 to 512 in SEQ ID 16, and
      (iii) effective, when hybridized to the processed human cFLIP transcript, to block expression of cFLIP in lymphocytes, and
   (b) covalently coupled to the antisense oligonucleotide compound, an arginine-rich peptide effective to enhance the uptake of the antisense compound into lymphocytes wherein said arginine-rich peptide has the sequence identified by SEQ ID NO: 2.

5. The conjugate of claim 4, wherein said antisense compound has a base sequence that is complementary to at least 12 contiguous bases extending from −12 to +12 bases with respect to the AUG start site in a processed human cFLIP transcript, corresponding to SEQ ID NO:4 in SEQ ID NO: 16.

6. The conjugate of claim 1, wherein said arginine-rich peptide has the sequence identified by SEQ ID NO:1 or 2.

7. The conjugate of claim 1, wherein the lymphocytes are naïve T-cells.

8. The conjugate of claim 1, wherein the lymphocytes are antigen-activated T-cells.

9. The conjugate of claim 4, wherein the morpholino subunits are joined by phosphorodiamidate linkages, in accordance with the structure:

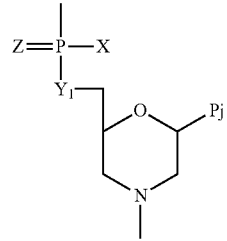

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino.

10. The conjugate of claim 9, wherein X=$NR_2$, where each R is independently hydrogen or methyl.

* * * * *